(12) United States Patent
Bender et al.

(10) Patent No.: US 8,202,674 B2
(45) Date of Patent: Jun. 19, 2012

(54) POLYMERS OF NAPTHALENE TETRACARBOXYLIC DIIMIDE DIMERS

(75) Inventors: Timothy P. Bender, Port Credit (CA); John Graham, Oakville (CA); James M. Duff, Mississauga (CA)

(73) Assignee: Xerox Corporation, Norwalk, CT (US)

( * ) Notice: Subject to any disclaimer, the term of this patent is extended or adjusted under 35 U.S.C. 154(b) by 0 days.

(21) Appl. No.: 12/901,682

(22) Filed: Oct. 11, 2010

(65) Prior Publication Data

US 2011/0028724 A1 Feb. 3, 2011

Related U.S. Application Data

(62) Division of application No. 12/478,981, filed on Jun. 5, 2009, now Pat. No. 7,820,780, which is a division of application No. 12/051,182, filed on Mar. 19, 2008, now Pat. No. 7,544,450, which is a division of application No. 11/140,386, filed on May 27, 2005, now Pat. No. 7,449,268.

(51) Int. Cl.
G03G 5/04 (2006.01)
C07D 221/18 (2006.01)
(52) U.S. Cl. .......................... 430/58.7; 546/76
(58) Field of Classification Search .............. 546/76; 430/58.7
See application file for complete search history.

(56) References Cited

U.S. PATENT DOCUMENTS

| | | | |
|---|---|---|---|
| 2,610,120 A | 9/1952 | Minsk et al. | |
| 2,670,284 A | 2/1954 | Zvanut | |
| 2,670,286 A | 2/1954 | Minsk et al. | |
| 3,007,901 A | 11/1961 | Minsk | |
| 3,180,730 A | 4/1965 | Klupfel et at | |
| 3,240,596 A | 3/1966 | Fox | |
| 3,245,833 A | 4/1966 | Trevoy | |
| 3,250,615 A | 5/1966 | Van Allan et al. | |
| 3,262,807 A | 7/1966 | Sterman et al. | |
| 3,274,000 A | 9/1966 | Noe et al. | |
| 3,542,547 A | 11/1970 | Wilson | |
| 3,567,450 A | 3/1971 | Brantly et al. | |
| 3,625,402 A | 12/1971 | Kulis | |
| 3,658,520 A | 4/1972 | Brantly et al. | |
| 3,880,657 A | 4/1975 | Rasch | |
| 4,127,412 A | 11/1978 | Rule et al. | |
| 4,150,987 A | 4/1979 | Anderson et al. | |
| 4,423,129 A | 12/1983 | Takasu et al. | |
| 4,446,217 A | 5/1984 | Takasu et al. | |
| 4,456,671 A | 6/1984 | Mabuchi et al. | |
| 4,481,271 A | 11/1984 | Hashimoto et al. | |
| 4,487,824 A | 12/1984 | Katagiri et al. | |
| 4,554,231 A | 11/1985 | Ishikawa et al. | |
| 4,666,802 A | 5/1987 | Hung et al. | |
| 4,701,396 A | 10/1987 | Hung et al. | |
| 4,727,139 A | 2/1988 | Hung et al. | |
| 5,266,429 A | 11/1993 | Sorriero et al. | |
| 5,468,583 A | 11/1995 | Gruenbaum et al. | |
| 5,814,426 A | 9/1998 | Fuller et al. | |
| 5,874,192 A | 2/1999 | Fuller et al. | |
| 5,882,814 A | 3/1999 | Fuller et al. | |
| 6,794,102 B2 | 9/2004 | Bender et al. | |
| 7,011,916 B2 | 3/2006 | Bender et al. | |
| 2005/0031977 A1 | 2/2005 | Kim et al. | |
| 2006/0210898 A1 | 9/2006 | Jubran | |

FOREIGN PATENT DOCUMENTS

JP 2005-126367 A 5/2005

OTHER PUBLICATIONS

Abstract of JP 2005-126367 published May 19, 2005.
Machine English Translation of JP 2005-126367 published May 19, 2005.

*Primary Examiner* — Hoa V Le

(74) *Attorney, Agent, or Firm* — Fay Sharpe LLP

(57) ABSTRACT

Polymers of naphthalene tetracarboxylic diimide dimmers are provided. The polymers are of the Formula I

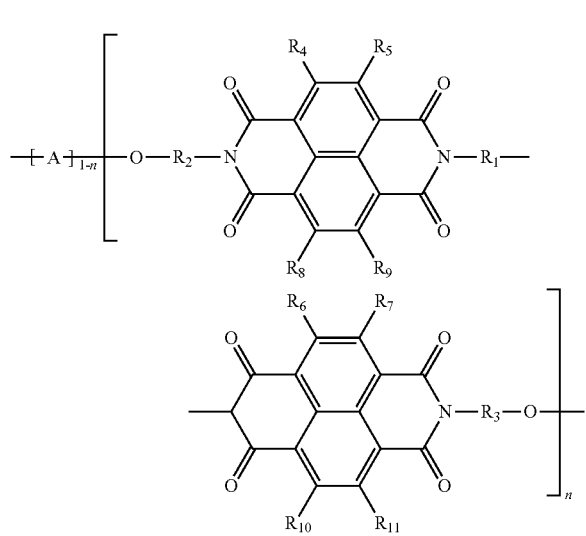
wherein the A units are selected from
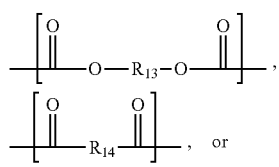, or
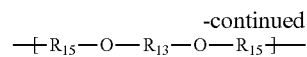
and Formula IX
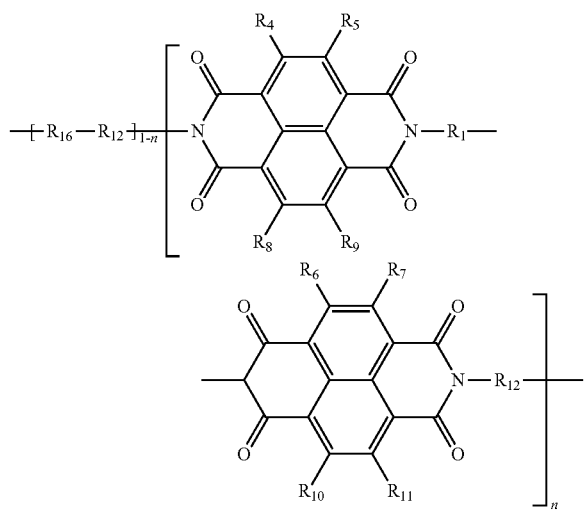
The polymers are suitable for use in the active layer of an imaging member and exhibit properties of both a binder and an electron-transporting material.
8 Claims, 8 Drawing Sheets

POLYMERS OF NAPTHALENE TETRACARBOXYLIC DIIMIDE DIMERS

This application is a divisional of U.S. patent application Ser. No. 12/478,981 filed Jun. 5, 2009, which is a divisional of U.S. patent application Ser. No. 12/051,182, filed Mar. 19, 2008, now U.S. Pat. No. 7,544,450, which is a divisional of U.S. patent application Ser. No. 11/140,386, filed May 27, 2005, now U.S. Pat. No. 7,449,268. These three applications are hereby incorporated herein in their entirety by reference.

BACKGROUND

Illustrated herein in various exemplary embodiments are polymer materials containing naphthalene tetracarboxylic diimide (NTDI) dimers. The polymer materials containing NTDI dimers are capable of functioning as both a binder and an electron-transporting material in an electrophotographic element. Also illustrated herein are electrophotographic or photoconductor elements that include such polymer materials. These materials find particular application in conjunction with xerographic and electrostatographic printing processes, and will be described with particular reference thereto. It is to be appreciated, however, that the present disclosure and exemplary embodiments are also amenable to other applications.

Many electrophotographic elements currently in use are designed to be initially charged with a negative polarity. Such elements contain a material that facilitates the migration of positive holes toward the negatively charged surface in imagewise exposed areas in order to cause imagewise discharge. Such a material is often referred to as a hole-transport agent. In electrophotographic elements of that type, a positively charged toner material is usually then used to develop the remaining imagewise undischarged areas of negative polarity potential, i.e., the latent image, into a toner image. Because of the wide use of negatively charging elements, considerable numbers and types of positively charging toners have been fashioned and are available for use in electrophotographic developers.

However, for some applications of electrophotography it is more desirable to be able to develop the surface areas of the element that have been imagewise exposed to actinic radiation, rather than those that remain imagewise unexposed. For example, in laser printing of alphanumeric characters it is more desirable to be able to expose the relatively small percentage of surface area that will actually be developed to form visible alphanumeric toner images, rather than waste energy exposing the relatively large percentage of surface area that will constitute undeveloped background portions of the final image. In order to accomplish this while still employing widely available high quality positively charging toners, it is necessary to use an electrophotographic element that is designed to be positively charged. Positive charging toner can then be used to develop the exposed surface areas, which will have, after exposure and discharge, relatively negative electrostatic potential compared to the unexposed areas, where the initial positive potential will remain. An electrophotographic element designed to be initially positively charged may contain an adequate electron-transport agent, that is, a material which facilitates the migration of photogenerated electrons toward the positively charged insulative element surface.

Electrophotographic elements include both those commonly referred to as single layer, or single-active-layer, elements and those commonly referred to as multiactive, multilayer, or multi-active-layer elements.

Single-active-layer elements are so named because they contain only one layer that is active both to generate and to transport charges in response to exposure to actinic radiation. Such elements typically comprise at least an electrically conductive layer in electrical contact with an active layer. In single-active-layer elements, the active layer contains a charge-generation material to generate electron/hole pairs in response to actinic radiation and an electron-transport and/or hole-transport agent, which comprises one or more of chemical compounds capable of accepting electrons and/or holes generated by the charge-generation material and transporting them through the layer to effect discharge of the initially uniform electrostatic potential. The active layer is electrically insulative except when exposed to actinic radiation, and it sometimes contains an electrically insulative polymeric film-forming binder, which may itself be the charge-generating material, or it may be an additional material that is not charge-generating. In either case, the transport agent(s) is (are) dissolved or dispersed as uniformly as possible in the layer.

Multiactive elements are so named because they contain at least two active layers, at least one charge generation layer (CGL) which is capable of generating charges, i.e., electron/hole pairs, in response to exposure to actinic radiation, and at least one charge transport layer (CTL) which is capable of accepting and transporting charges generated by the charge-generation layer. Such elements typically comprise at least an electrically conductive layer, a CGL, and a CTL. Either the CGL or the CTL is in electrical contact with both the electrically conductive layer and the remaining CTL or CGL. The CGL contains at least a charge-generation material; the CTL contains at least a charge-transport agent; and either or both layers can contain an electrically insulative film-forming polymeric binder.

In multiactive, positively charged photoconductor elements of the type employing at least a CGL and a CTL, the CTL may be the uppermost layer of the element to protect the more mechanically sensitive CGL from wear. Known electron-transport agents may suffer from one or more problems upon repeated use, such as high dark decay, insufficient electronic charge transport activity, a gradually increasing residual potential or the like. Certain electron-transport agents, such as trinitrofluorenone (TNF), which do exhibit a useful level of sensitivity, suffer from the further disadvantage that they are now suspected to be carcinogens.

As mentioned, in both single-active-layer elements and multiactive layer elements, the transporting materials, such as electron-transport materials and hole transport materials, are typically dispersed in a polymeric binder. In particular, the transporting materials may be dispersed as a solid state solution in a polymeric binder material. Generally, device performance may be increased by increasing the concentration of the respective transport materials in a given active layer element. The concentration of the transport materials, however, is limited by the solubility of the transport materials in the binder. A single-layer photoreceptor, for example, typically comprises about 48 wt % of a polymeric binder, 30 wt % of a hole-transporting molecule, 20 wt % of an electron-transporting molecule, and 2 wt % of a charge generating material, such as a charge generating pigment. This, however, appears to be the upper limit for the concentrations of the respective components to form a solid state solution without crystallization of the transport molecules and/or loss of mechanical integrity of the device.

Thus, there is a need to provide materials that will allow for an increase in the concentrations of the transport materials in an active layer of a photoreceptor and still form a solid state solution. One way to achieve such a result would be to provide materials that have dual functionalities, i.e., function as both a binder and a transport material. U.S. Pat. Nos. 5,814,426; 5,874,192; and 5,882,814, the entire disclosures of which are incorporated herein by reference, disclose hole transport materials that also function as binder materials. U.S. Pat. No. 5,266,429 is directed to a polyesterimide that includes a dioxy component and a dicarbonyl component, one of which contains a tetracarbonyldiimide group. The polyesterimide in U.S. Pat. No. 5,266,429 may be used as a binder layer or may be the sole material in a charge transport layer.

As between electron-transporting materials and hole-transporting materials, hole-transporting materials are generally more compatible with polymeric binder materials. That is, hole-transporting materials will form a solid state solution over a wider concentration range than will electron-transport materials. Therefore it is desirable to provide a hybrid material that is capable of function as a binder material and an electron-transporting material.

BRIEF DESCRIPTION

In one aspect, provided herein in one embodiment is an A compound of the Formula I:

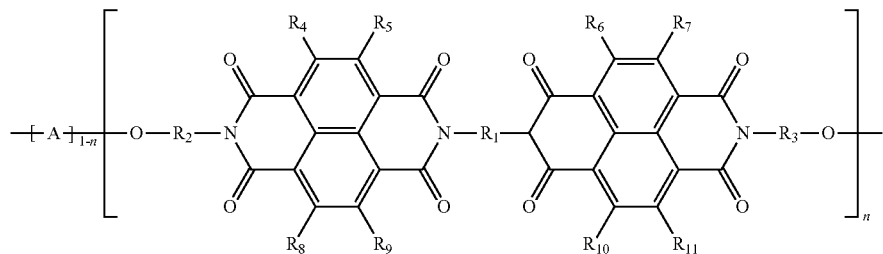

wherein:
the A unit is selected from the group consisting of:

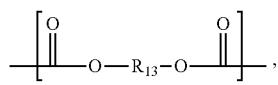

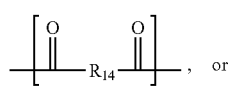, or

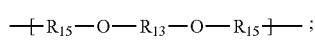;

$R_1$ is independently selected from the group consisting of a hetero atom containing group and a hydrocarbon group that is optionally substituted at least once with a hetero atom moiety;

$R_2$ and $R_3$ are independently selected from the group consisting of a hydrocarbon group and a substituted hydrogen group;

$R_4$, $R_5$, $R_6$, $R_7$, $R_8$, $R_9$, $R_{10}$, and $R_{11}$ are independently selected from the group consisting of a nitrogen containing group, a sulfur containing group, a hydroxyl group, a silicon containing group, hydrogen, a halogen, a hetero atom containing group, a hydrocarbon group and a substituted hydrocarbon group;

$R_{13}$ is selected from the group consisting of

 (a)

 (b)

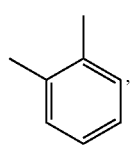 (c)

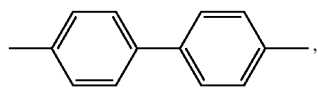 (d)

-continued

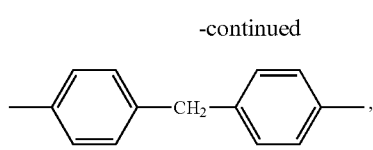 (e)

(f)

(g)

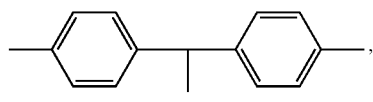

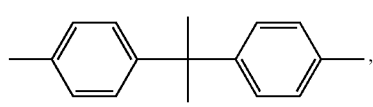

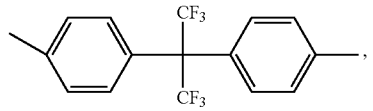 (h)

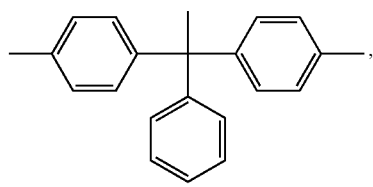 (i)

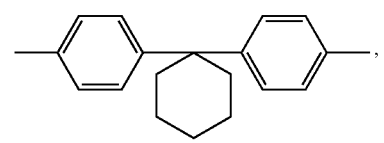 (j)
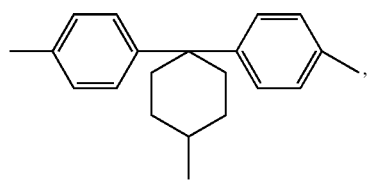 (k)
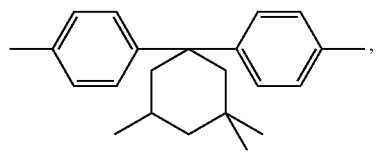 (l)
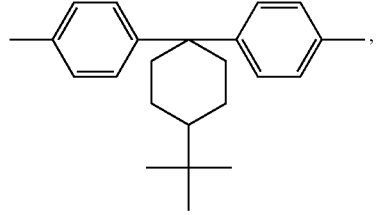 (m)
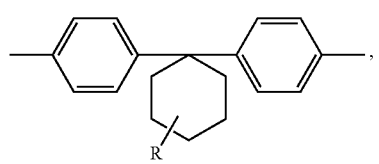 (n)
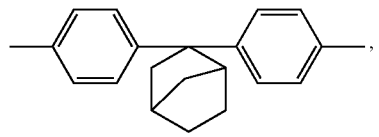 (o)
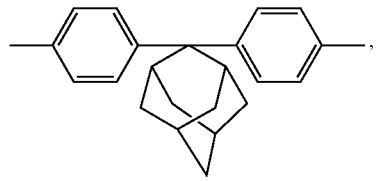 (p)
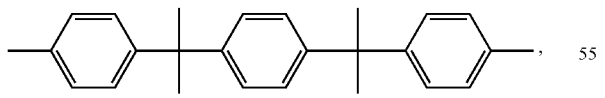 (q)
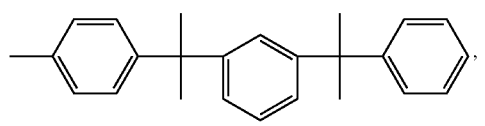 (r)
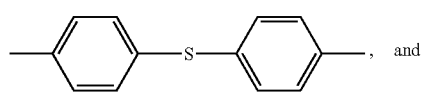 and (s)
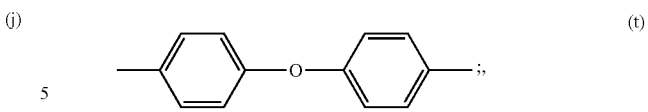 ; (t)
$R_{14}$ is selected from the group consisting of a hydrocarbon group and a substituted hydrocarbon; and
$R_{15}$ is selected from the group consisting of
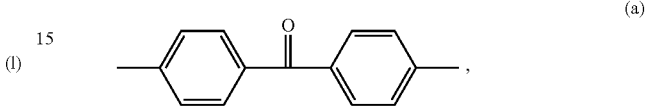 (a)
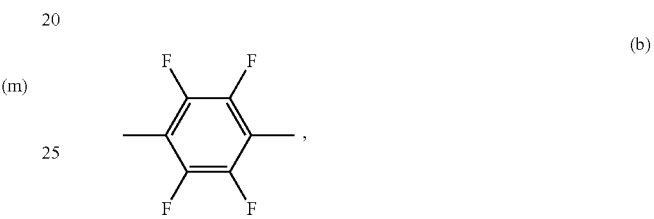 (b)
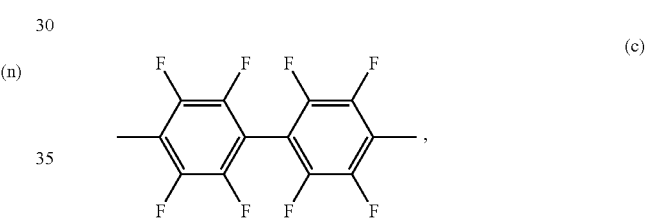 (c)
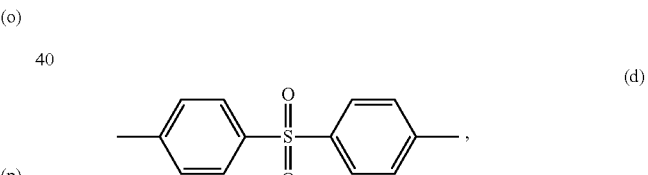 (d)
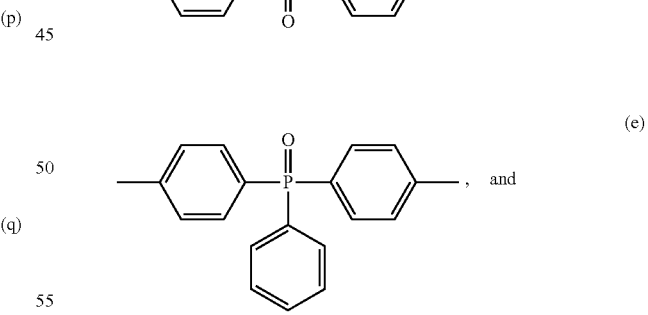 and (e)
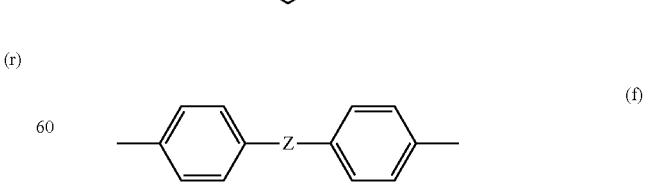 (f)
wherein Z is an electron withdrawing group.

In another aspect, the present disclosure provides: an A compound of Formula IX

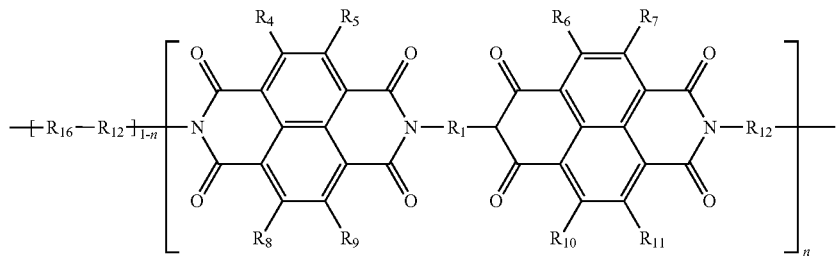

wherein $R_1$ is independently selected from the group consisting of a hetero atom containing group, a hydrocarbon containing group, and a hydrocarbon group substituted at least once with a hetero atom moiety;

$R_{12}$ is independently selected from the group consisting of a nitrogen containing group, a sulfur containing group, a hydroxyl group, a silicon containing group, hydrogen, a halogen, a hetero atom containing group, a hydrocarbon group and a substituted hydrocarbon group;

$R_{16}$ is selected from:

(a)
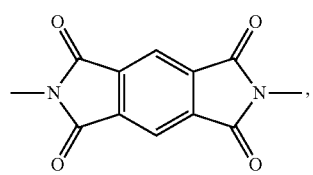

(b)
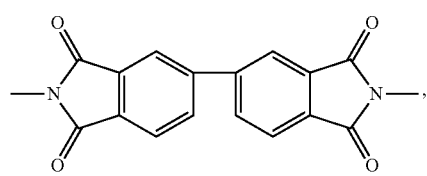

(c)
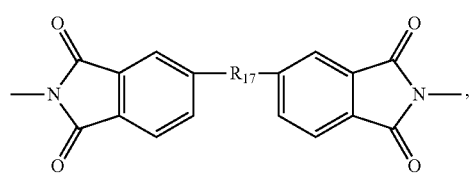

(d)
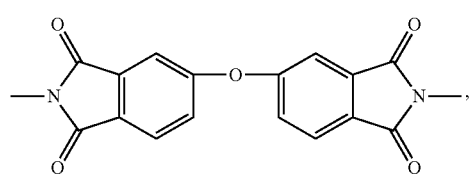

(e)
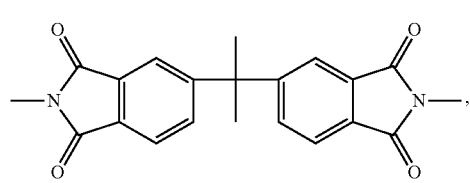

-continued (f)
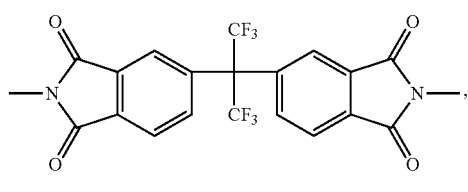

(g)
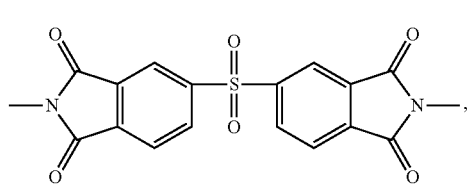

(h)
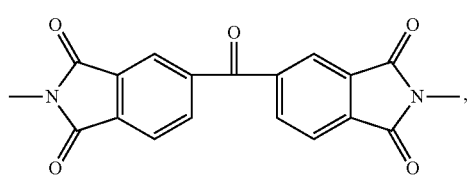

(i)
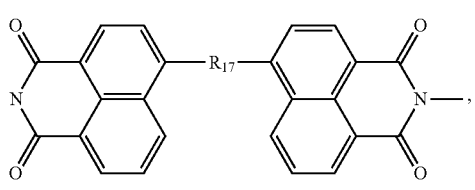

(j)
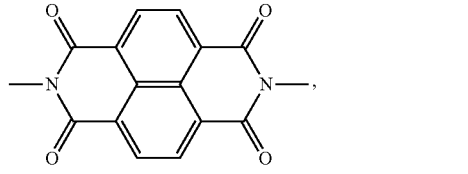

(k)
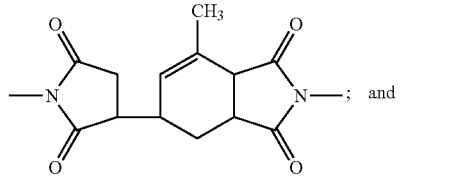

; and wherein $R_{17}$ is independently selected from the group consisting of a nitrogen containing group, a sulfur containing group, a hydroxyl group, a silicon containing group, hydrogen, a halogen, a hetero atom containing group, a hydrocarbon group and a substituted hydrocarbon group;

and

R$_4$, R$_5$, R$_6$, R$_7$, R$_8$, R$_9$, R$_{10}$, and R$_{11}$ are independently selected from the group consisting of a nitrogen containing group, a sulfur containing group, a hydroxyl group, a hydrocarbon group, and a hydrocarbon group that is substituted at least once with a hetero atom moiety.

In still another aspect, the present disclosure provides:
a photoconductive imaging member comprising
a substrate, and
a single active layer formed over the substrate, the single active layer comprising a mixture of a photogenerating component, a hold transport material, and a polymer material selected from a polymer of the Formula I

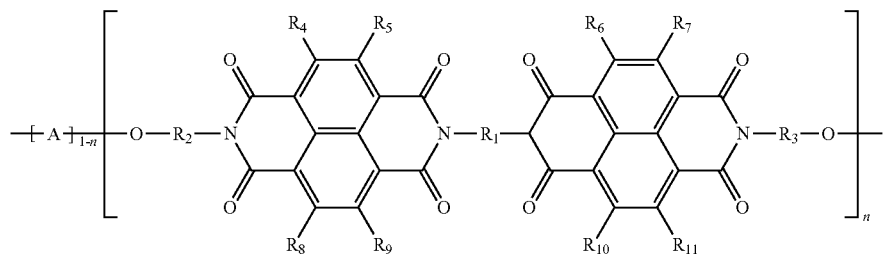

and a polymer of the Formula IX

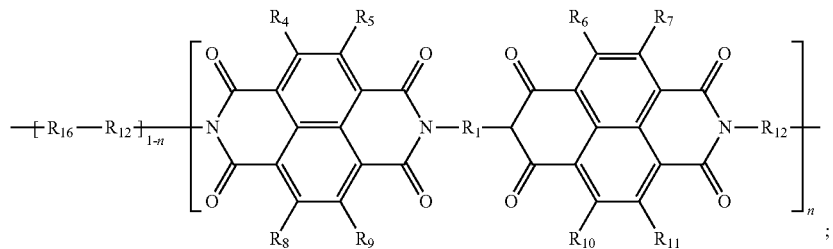

wherein A is selected from the group consisting of

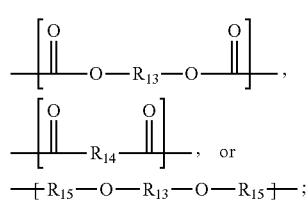

R$_1$ is independently selected from the group consisting of a hetero atom, containing group, a hydrocarbon group, and a hydrocarbon group substituted at least once with a hetero atom moiety;

R$_2$ and R$_3$ are independently selected from the group consisting of a hydrocarbon group or a substituted hydrocarbon group;

R$_4$, R$_5$, R$_6$, R$_7$, R$_8$, R$_9$, R$_{10}$, and R$_{11}$ are independently selected from the group consisting of a nitrogen containing group, a sulfur containing group, a hydroxyl group, a silicon containing group, hydrogen, a halogen, a hetero atom containing group, a hydrocarbon group, and a hydrocarbon group substituted at least once with a hetero atom moiety;

R$_{12}$ is independently selected from the group consisting of a nitrogen containing group, a sulfur containing group, a hydroxyl group, a silicon containing group, hydrogen, a halogen, a hetero atom containing group, a hydrocarbon group and a substituted hydrocarbon group;

R$_{13}$ is selected from the group consisting of

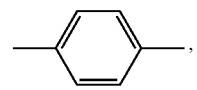
(a)

-continued

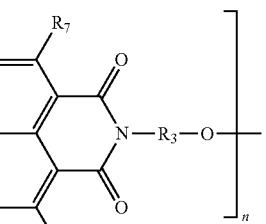
(b)

(c)

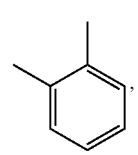
(d)

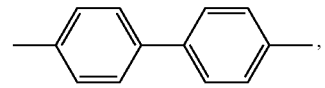
(e)

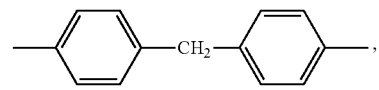
(f)

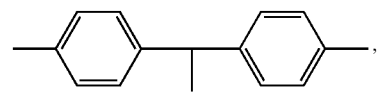

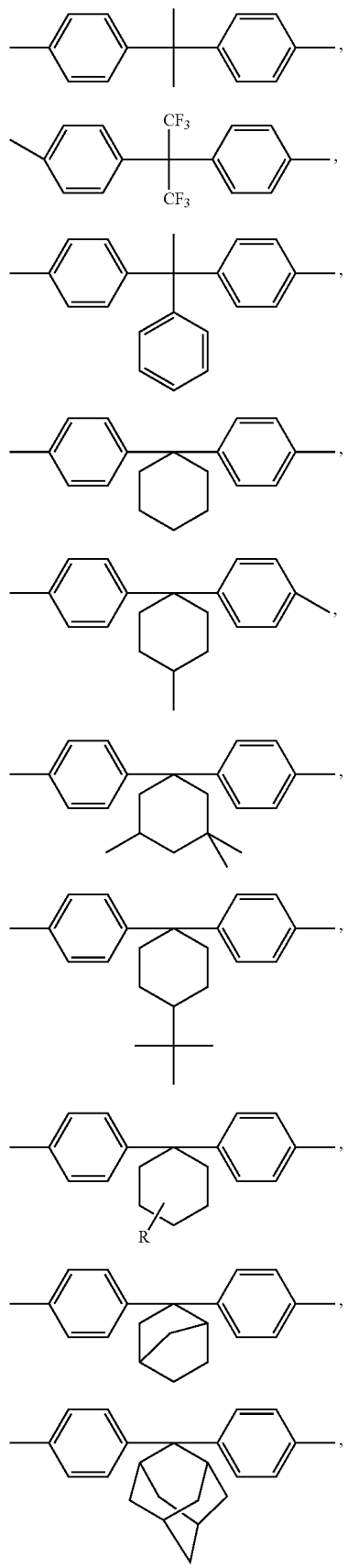
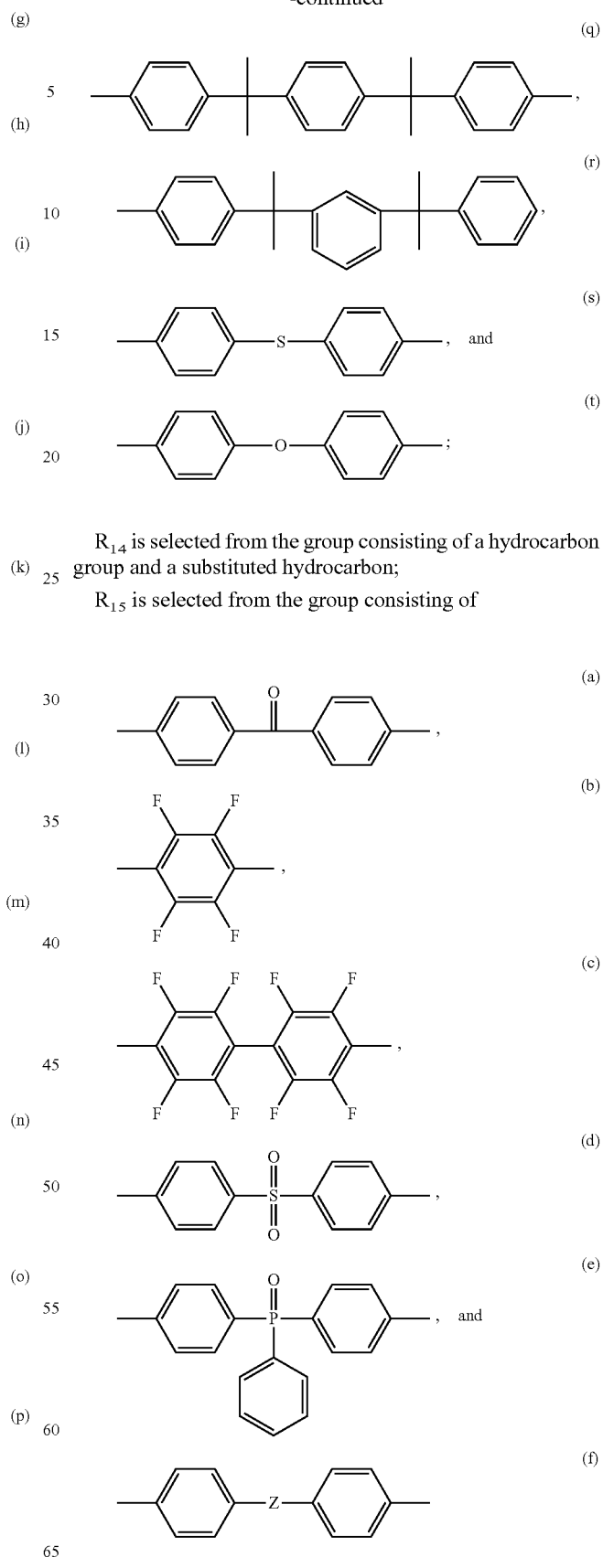
$R_{14}$ is selected from the group consisting of a hydrocarbon group and a substituted hydrocarbon;
$R_{15}$ is selected from the group consisting of
wherein Z is an electron withdrawing group;

$R_{16}$ is selected from the group consisting of

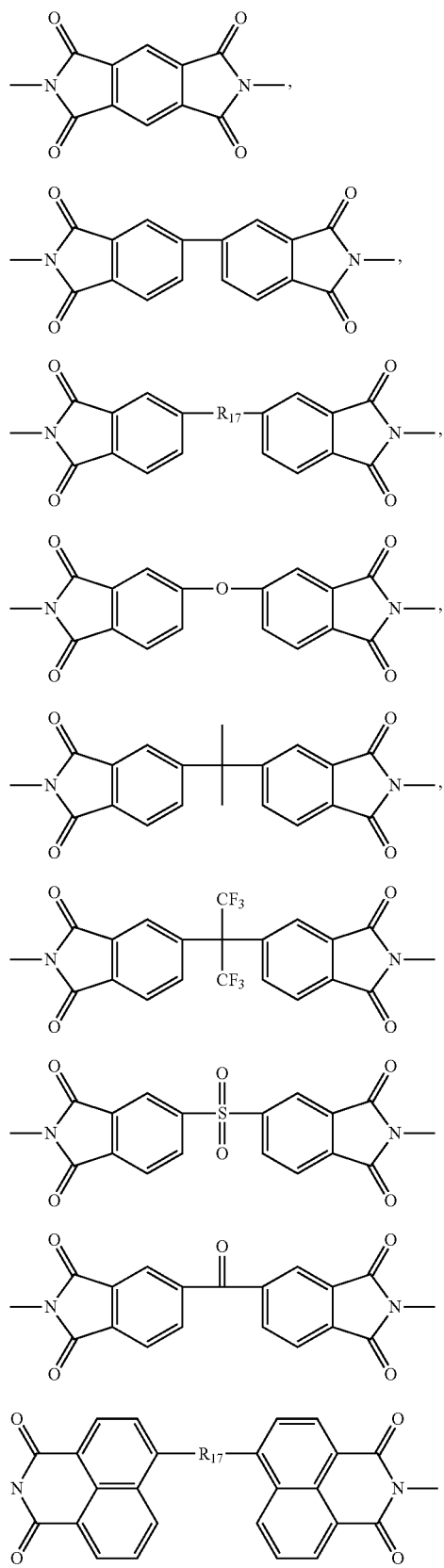

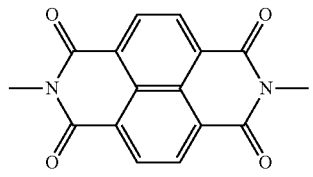

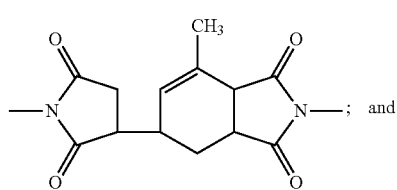

Wherein $R_{17}$ is independently selected from the group consisting of a nitrogen containing group, a sulfur containing group, a hydroxyl group, a silicon containing group, hydrogen, a halogen, a hetero atom containing group, a hydrocarbon group and a substituted hydrocarbon group; and n is a fraction between 0 and 1.

In yet another aspect, the present disclosure provides a photoimaging member comprising a substrate; a charge generating layer; and a charge transport layer, wherein said charge transport layer comprises a polymer composition comprising a naphthalene tetracarboxylic diimide dimer component.

BRIEF DESCRIPTION OF THE DRAWINGS

Unless otherwise noted, the same reference numeral in different Figures or Formulas described or illustrated herein refers to the same or similar feature.

DETAILED DESCRIPTION

Figure 1:
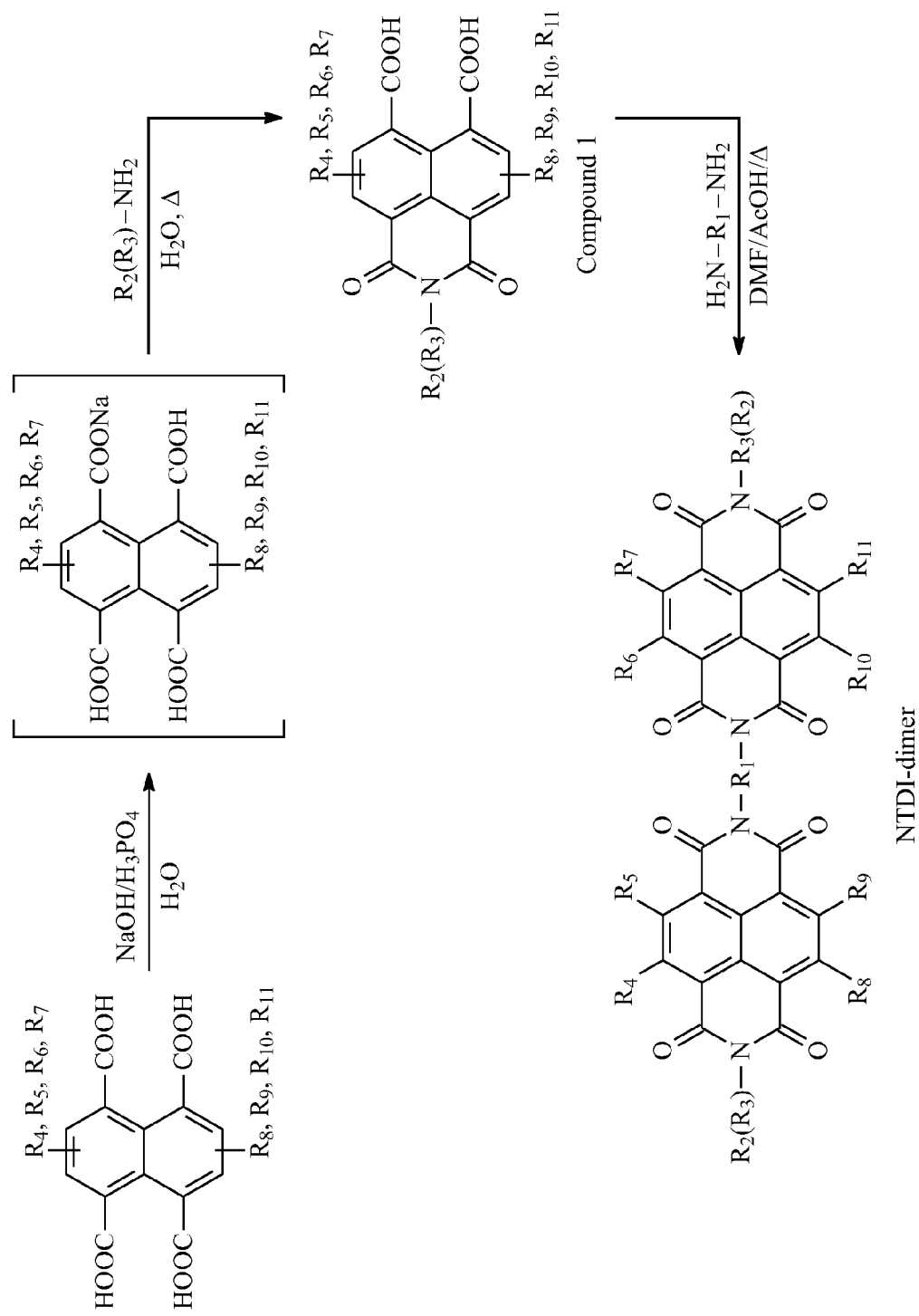
FIG. 1 depicts a first illustrative synthesis route for preparing dihydroxy naphthalene tetracarboxylic diimide dimers.

Illustrated herein, in various exemplary embodiments, are polymer materials that are capable of functioning as a polymer binder material and an electron transporting material in an active layer of a photoconductor. In particular, the polymer materials comprise naphthalene tetracarboxylic diimide dimers. In embodiments, the polymeric materials may be represented as a compound of the Formula I:

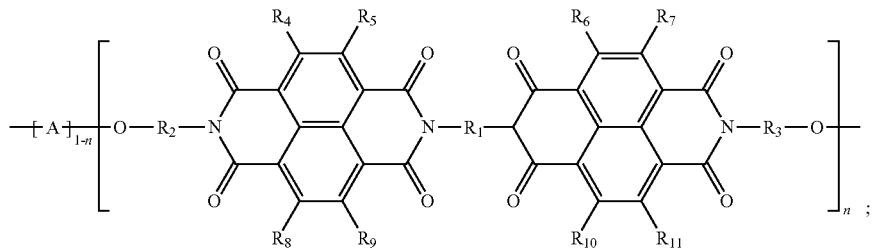

wherein n= is a fraction between 0 and 1.

Compounds of Formula I are generally polymer materials that include a base polymer unit or component, such as repeating unit A in Formula I, and a naphthalene tetracarboxylic diimide dimer component. In embodiments, compounds of the Formula I are polycarbonates, polyesters, or polyarylethers having a naphthalene tetracarboxylic diimide dimer component. Component A is referred to herein as the binder or resin component.

The naphthalene tetracarboxylic diimide dimer component comes from naphthalene tetracarboxylic diimide dimers. Naphthalene tetracarboxylic diimide dimers are described in co-pending application Ser. No. 10/197,933, published as U.S. Patent Application Publication No. 2004/0013959, the entire disclosure of which is incorporated herein by reference. An example of naphthalene tetracarboxylic diimide dimer include the dihydroxyl form as represented by the compound of Formula II:

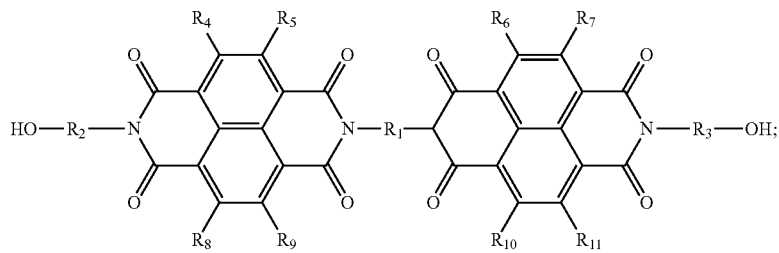

wherein n= is a fraction between 0 and 1.

The substituent $R_1$ is independently selected from the group consisting of a hetero atom containing group and a hydrocarbon group that is optionally substituted at least once with a hetero atom moiety. As used herein, the phrase hetero atom containing group indicates that there is present at least one other type of atom other than carbon and hydrogen within the group and that the hetero atom or hetero atoms are part of the main structural chain of the group, such as, for example, 3-oxa-pentan-1,5-diyl. As used herein, the phrase hetero atom moiety indicates that there is present at least one other type of atom other than carbon and hydrogen within the group and that the hetero atom moiety is not part of the main structural chain of the group, such as, for example 2-hydroxypropan-1,3-diyl. The term hydrocarbon refers to any moiety composed of carbon atoms and hydrogen atoms. The hydrocarbon may optionally be a substituted hydrocarbon where one or more of the hydrogen atoms are replaced with another substituent. Furthermore, the term hydrocarbon includes for instance acyclic hydrocarbons, alicyclic hydrocarbons, aromatic hydrocarbons and the like which may be optionally substituted.

Examples of moieties suitable as the hetero atom containing group (for $R_1$) include, but are not limited to, (a) an alkoxy group having from about 3 to about 30 atoms, and in embodiments from about 3 to about 6 atoms such as, for example, 3-oxa-pentan-1,5-diyl, an aldehyde group, and a ketone group; (b) a heterocyclic system having from about 11 to about 30 atoms such as, for example, N-phenylcarbazol-3,5-diyl; and (c) an alkoxyaryl having from about 7 to about 30 atoms such as, for example, 2-methoxybenzen-1,4-diyl and 2-ethoxybenzen-1,4-diyl.

Examples of the hydrocarbon group (for $R_1$) include, but are not limited to, (a) a straight chain alkyl group having from about 1 to about 30 carbon atoms, and in embodiments from 1 to about 6 carbon atoms, such as, for example, ethan-1,2-diyl, butan-1,4-diyl, hexan-1,6-diyl, and the like; (b) a branched alkyl group having from about 3 to about 30 carbon atoms, and in embodiments from about 3 to about 6 carbon atoms such as, for example, 2-methylpentan-1,5-diyl and 2,2-dimethylpropan-1,3-diyl; (c) a cycloalkyl group having from about 3 to about 20 carbon atoms, and in embodiments from 4 to about 6 carbon atoms such as, for example, cyclopentan-1,3-diyl and cyclohexan-1,4-diyl; (d) a monocyclic aromatic group such as, for example, phenyl like benzen-1,2-diyl, benzen-1,3-diyl and benzen-1,4-diyl; (e) a polycyclic aromatic group having from about 11 to about 30 carbon atoms such as, for example, naphthyl (e.g., naphthalen-1,5-diyl and naphthalene-2,7-diyl) and anthracen-9,10-diyl; (f) an alkylaryl group having from about 7 to about 30 carbon atoms such as, for example, p-xylen-α,α-diyl; and (g) an arylalkyl group having from about 7 to about 30 carbon atoms such as, for example, 2,5-diisopropylbenzen-1,4-diyl.

Any of the hydrocarbon groups can be optionally substituted one, two, or more times with the same or a different substituting moiety including, but not limited to, (a) a nitrogen containing group such as, for example, amino and nitro; (b) a sulfur containing group such as, for example, thiol, sulfoxide, sulfate, chlorosulfate and the like; (c) a hydroxyl group; (d) a silicon containing group such as, for example, a trisubstituted silane where the substituent is a hydrocarbon; (e) a halogen such as, for example, bromine, chlorine, fluorine, and iodine; and (f) a hetero atom moiety, having about 3 to about 15 atoms, and including an element selected from the group consisting of, for example, nitrogen, sulfur, silicon, and oxygen, such as, for example, thiophen-2-yl, thiophen-3-yl, pyridin-2-yl, pyridin-3-yl, pyridin-4-yl, furan-2-yl, furan-3-yl and the like. Non-limiting examples of suitable substituted hydrocarbon groups include, but are not limited to, the following: 3-hydroxyhexan-1,6-diyl; 2-methylbenzen-1,4-diyl; and 2,5-dimethylbenzen-1,4-diyl.

For reasons further described herein, with respect to the naphthalene tetracarboxylic diimide dimers used in the present disclosure, $R_2$ and $R_3$ are independently selected from the group consisting of substituted hydrocarbon groups. In particular, $R_2$ and $R_3$ are hydroxyl substituted hydrocarbon groups such as shown in Formula II. Examples of suitable hydroxyl substituted hydrocarbon groups include, but are not limited to, straight chain alkyl groups having from about 1 to about 30 carbon atoms, branched alkyl groups having from about 3 to about 30 carbon atoms, cycloalkyl groups having from about 3 to about 20 carbon atoms, monocyclic aromatic groups having such as, for example, phenyl and benzenyl, polycyclic aromatic groups having from about 11 to about 30 carbon atoms, alkylaryl groups having from about 7 to about 30 carbon atoms, and arylalkyl groups having from about 7 to about 30 carbon atoms. In embodiments, $R_2$ and $R_3$ may be different hydrocarbons groups. In other embodiments, $R_2$ and $R_3$ are the same hydrocarbon group.

$R_4$, $R_5$, $R_6$, $R_7$, $R_8$, $R_9$, $R_{10}$, and $R_{11}$ may be independently selected from the group consisting of a nitrogen containing group, a sulfur containing group, a hydroxyl group, a silicon containing group, hydrogen, a halogen (e.g., bromine, chlorine, fluorine, and iodine), a hetero atom containing group and a hydrocarbon group that is optionally substituted at least once with a hetero atom moiety.

Examples of suitable hetero atom containing group (for $R_4$ through $R_{11}$) include but are not limited to, (a) an alkoxy group having about 3 to about 30 atoms, and, in embodiments, from about 3 to about 6 atoms such as, for example, 3-oxa-butan-1-yl, 4-methyl-3-oxapent-1-yl, an aldehyde group, and a ketone group; (b) a heterocyclic system having, for example, 11 to about 30 atoms such as N-phenylcarbazol-3-yl, thiophen-2-yl, thiophen-3-yl, pyridin-2-yl, pyridin-3-yl, pyridin-4-yl, furan-2-yl, furan-3-yl and the like; (c) an alkoxyaryl having about 7 to about 30 atoms such as, for example, 4-methoxybenzen-1-yl and 4-ethoxybenzen-1-yl; and (d) an arylalkoxy having about 7 to about 30 atoms such as, for example, 3-oxa-3-phenylpropan-1-yl; and (e) an aryloxy having about 7 to about 30 atoms such as, for example, 3-methylphenoxy, 4-nonylphenoxy, 1-naphthoxy and 2-naphthoxy.

Examples of compounds suitable as the hydrocarbon group (for $R_4$ through $R_{11}$) include, but are not limited to, (a) a straight chain alkyl group having 1 to about 30 carbon atoms, and in embodiments 1 to about 4 carbon atoms, such as, for example, ethanyl and butanyl; (b) a branched alkyl group having about 3 to about 30 carbon atoms, and in embodiments about 3 to about 4 carbon atoms such as, for example, 1-methylpropan-1-yl, 1-methylethan-1-yl and 1-methylmethan-1-yl; (c) a cycloalkyl group having about 3 to about 20 carbon atoms, and in embodiments 4 to about 6 carbon atoms such as, for example, cyclopentanyl and cyclohexanyl; (d) a monocyclic aromatic group such as, for example, phenyl like benzenyl; (e) a polycyclic aromatic group having about 11 to about 30 carbon atoms such as, for example, naphthyl (e.g., naphthalene-1-yl and naphthalene-2-yl) and anthracen-9-yl; (f) an alkylaryl group having about 7 to about 30 carbon atoms such as toluen-α-yl; and (g) an arylalkyl group having about 7 to about 30 carbon atoms such as 4-ethylbenzen-1-yl and 4-sec-butylbenzen-1-yl.

Examples of suitable moieties substitutions on the hydrocarbon group (any of the hydrocarbon groups can be optionally substituted one, two, or more times with the same or different substituting moiety) and of substituents for $R_4$, $R_5$, $R_6$, $R_7$, $R_8$, $R_9$, $R_{10}$, and $R_{11}$ include, but are not limited to, (a) a nitrogen containing group such as, for example, amino and nitro; (b) a sulfur containing group such as, for example, thiol, sulfoxide, sulfate, chlorosulfate; (c) a hydroxyl group; (d) a silicon containing group such as, for example, a trisubstituted silane where the substituent is a hydrocarbon; (e) a halogen such as, for example, bromine, chlorine, fluorine, and iodine; and (f) a hetero atom moiety, having, for example, about 3 to about 15 atoms, and including an element selected, for instance, from the group consisting of nitrogen, sulfur, silicon, and oxygen, such as, for example, thiophen-2-yl, thiophen-3-yl, pyridin-2-yl, pyridin-3-yl, pyridin-4-yl, furan-2-yl, furan-3-yl and the like. Examples of suitable substituted hydrocarbon groups include, but are not limited to, for instance: 2-hydroxyethan-1-yl, 3-hydroxypropan-1-yl, 2-methylbenzen-1-yl, 2,6-diisopropylbenzen-1-yl, 2,5-dimethylbenzen-1-yl, 4-methylnapthalen-1-yl, and 5-methylnaphthalen-2-yl.

As previously described herein, in embodiments, the base polymer component, i.e., component A in Formula I, may be a polycarbonate, a polyester, or a polyarylether. Polycarbonate, polyester, and polyarylether components are represented as follows in Formulas III-V, respectively:

Formula III

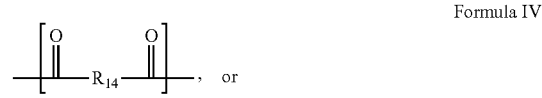

Formula IV

, or

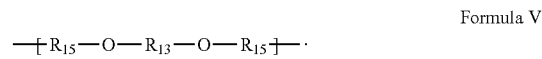

Formula V

In embodiments where the compound of Formula I is a polycarbonate, the A component is a repeating unit as shown in Formula III, and the compound has a structure as shown in Formula VI:

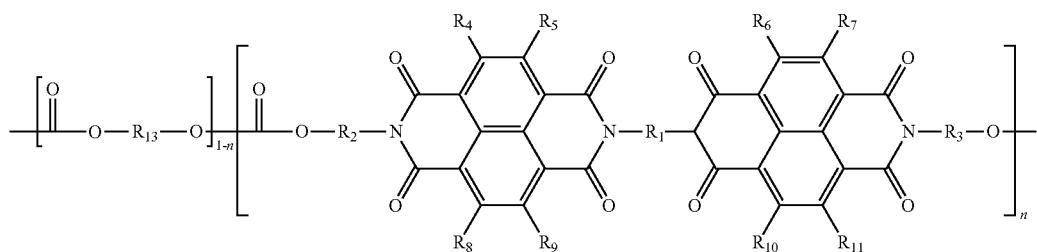
wherein n is a fraction between 0 and 1. Non-limiting examples of groups suitable as the R13 group include:
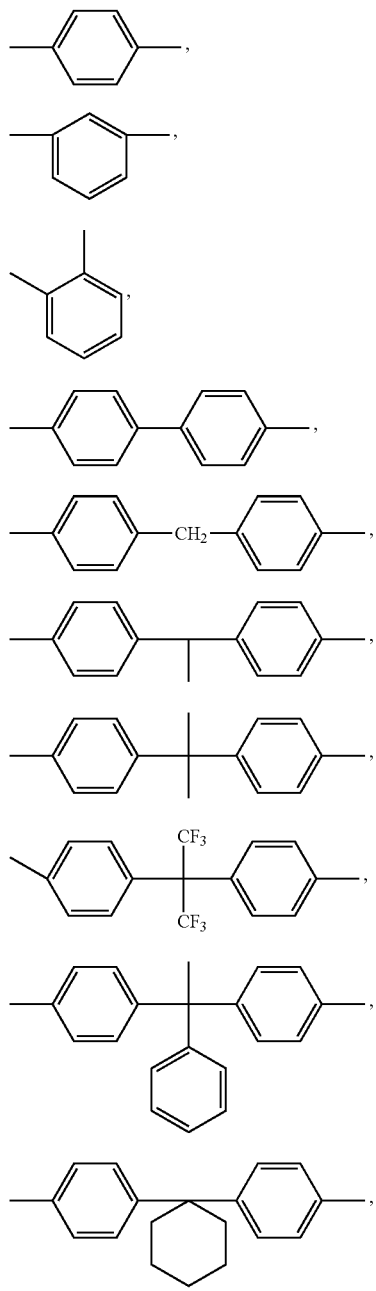

-continued

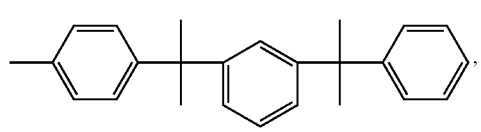
(r)

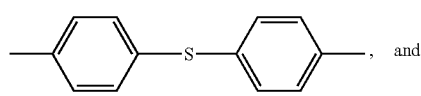
(s) , and

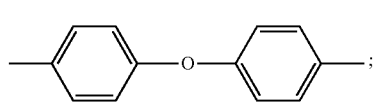
(t)

In embodiments where the compound of Formula I is a polyester, the A component is a repeating unit as shown in Formula IV, and the compound has a structure as shown in Formula VII:

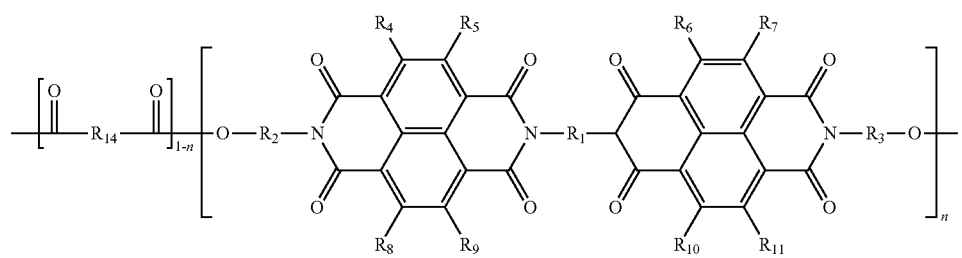

wherein n is a fraction between 0 and 1. $R_{14}$ may be chosen from the group of hydrocarbon and substituted hydrocarbon. Examples of suitable hydrocarbon groups include, but are not limited to, straight chain alkyl groups having from about 1 to about 30 carbon atoms, branched alkyl groups having from about 3 to about 30 carbon atoms, cycloalkyl groups having from about 3 to about 20 carbon atoms, monocyclic aromatic groups such as, for example, phenyl and benzenyl, polycyclic aromatic groups having from about 11 to about 30 carbon atoms, alkylaryl groups having from about 7 to about 30 carbon atoms, and arylalkyl groups having from about 7 to about 30 carbon atoms. Where $R_{14}$ is a substituted hydrocarbon, suitable substituting moieties include, but are not limited to, a nitrogen containing group, a sulfur containing group, a hydroxyl group, a silicon containing group, a halogen, or a hetero atom moiety having, for example, about 3 to about 15 carbon atoms and including an element selected from the group consisting of nitrogen, sulfur, silicon, and oxygen.

In other embodiments, compounds of the Formula I are a polyarylether. In such compounds, the repeating unit A is of a type as shown in Formula V, and the compound has a structure of Formula VIII:

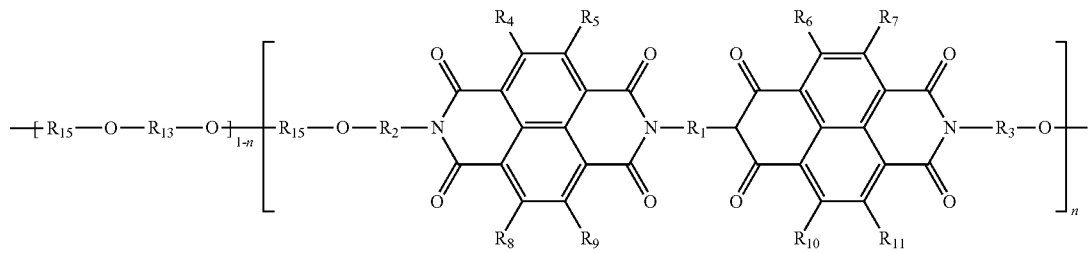

wherein n is a fraction between 0 and 1. In embodiments, $R_{15}$ is selected from moieties including, for example:

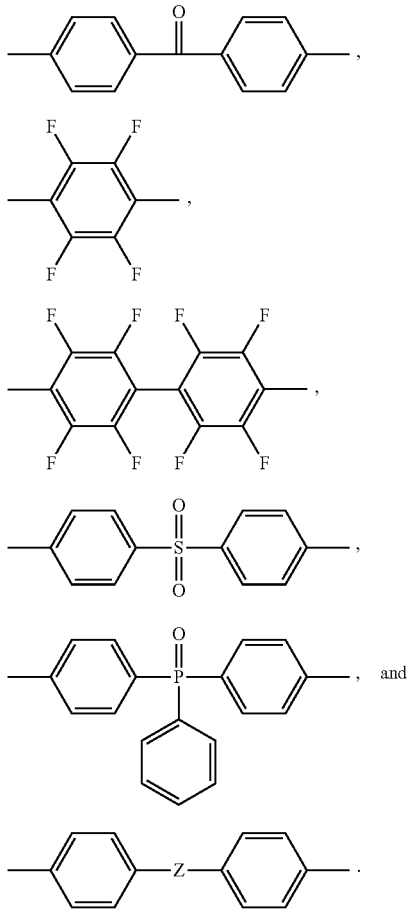

In embodiments, Z is an electron withdrawing group. Additionally, $R_{13}$ may be those moieties previously described herein as suitable for $R_{13}$ with respect to the polycarbonate polymers.

Figure 2:
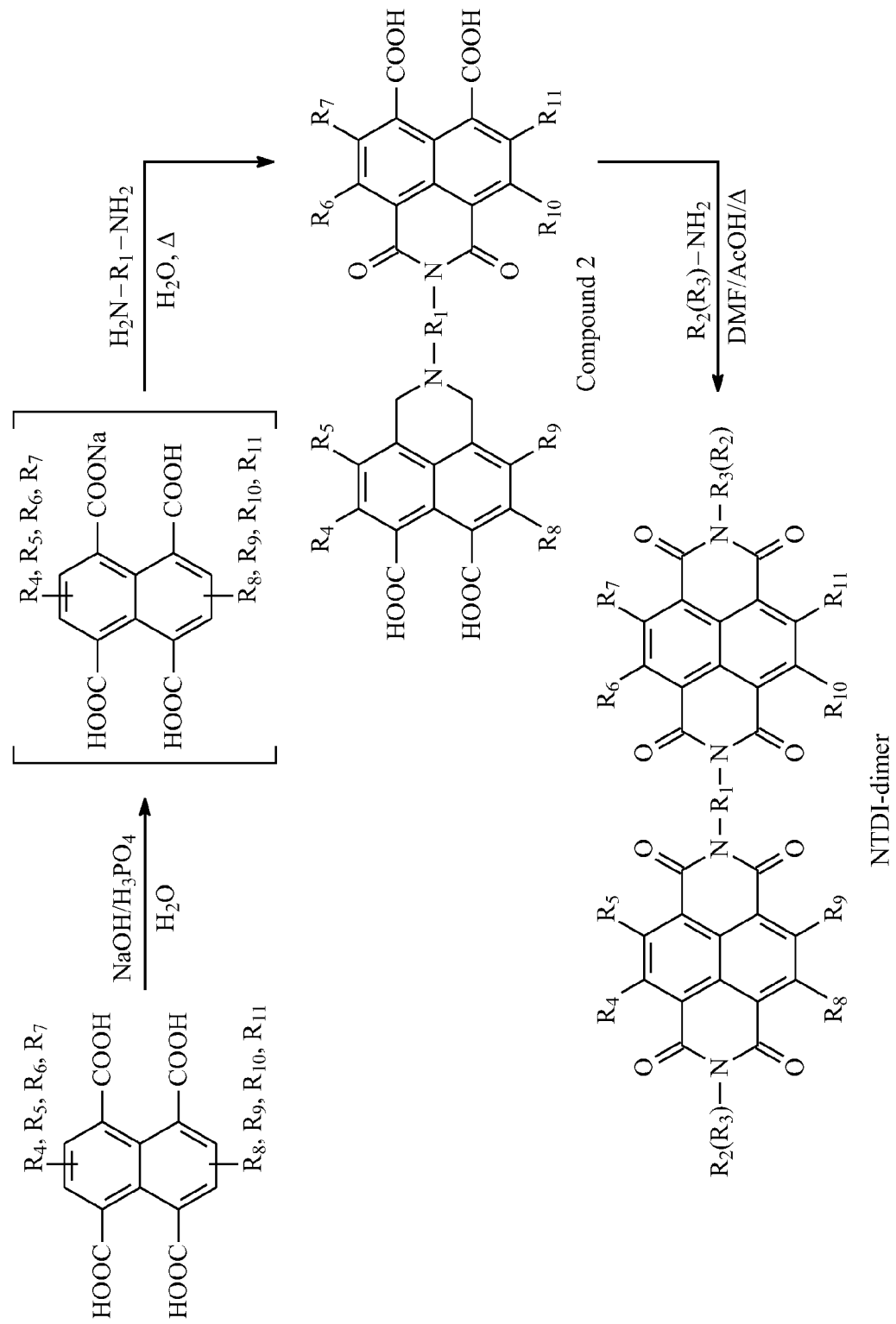
FIG. 2 depicts a second illustrative synthesis route for preparing dihydroxy naphthalene tetracarboxylic diimide dimers.

Polymer materials of the Formula I are generally formed by the reaction of a dihydroxy naphthalene tetracarboxylic diimide dimer and a polycarbonate, polyester, or polyarylether component. FIGS. 1 and 2 depict illustrative synthesis routes to prepare the dihydroxy naphthalene tetracarboxylic diimide dimer component. In FIGS. 1 and 2, $R_2$ and $R_3$ are shown as "$R_2(R_3)$" in the final compound and the reagents because the depicted synthesis pathways are primarily for the situation where $R_2$ and $R_3$ are symmetrical, i.e., they are the same. However, the present disclosure also encompasses the preparation of unsymmetrical compounds where $R_2$ and $R_3$ are different from each other.

The synthesis of symmetrical dihydroxy naphthalene tetracarboxylic diimide dimers (where $R_2$ and $R_3$ are the same) can be accomplished by a multi-step synthesis starting from 1,4,5,8-naphthalenetetracarboxylic acid or dianhydride by either of two routes. In the first route, as depicted in FIG. 1, a 1,4,5,8-naphthalene tetracarboxylic diimide dimer is synthesized as follows: 1,4,5,8-naphthalene tetracarboxylic acid or dianhydride is dissolved in aqueous alkali which is then treated sequentially with concentrated phosphoric acid, an aliphatic or alicyclic hydroxyl substituted monofunctional amine and heated to 90° C. for a period of time. Any insoluble material is filtered after which concentrated phosphoric acid is added to precipitate the product which can be collected, further purified and dried to remove residual water. Reaction of this material with a difunctional amino compound (such as 1,4-diaminobutane or 2,2-dimethyl-1,3-propane diamine) at elevated temperature in a suitable solvent (such as N,N-dimethylformamide, N,N-dimethylacetamide, quinoline, m-cresol, acetic acid and the like and mixtures thereof) yields a dihydroxy 1,4,5,8-naphthalene tetracarboxylic diimide dimer on isolation and purification.

In the second route, as depicted in FIG. 2, a 1,4,5,8-naphthalene tetracarboxylic diimide dimer is synthesized as follows: 1,4,5,8-naphthalene tetracarboxylic acid or dianhydride is dissolved in aqueous alkali which is then treated sequentially with concentrated phosphoric acid, a difunctional amine (such as 1,4-diaminobutane or 2,2-dimethyl-1,3-propane diamine) and heated to 90° C. for a period of time. Any insoluble material is filtered after which concentrated phosphoric acid is added to precipitate the product which can be collected, further purified and dried to remove residual water. Reaction of this material with an aliphatic or alicyclic hydroxyl substituted monofunctional amino compound (such as 4-aminobutane or 4-aminopentane) at elevated temperature in a suitable solvent (such as N,N-dimethylformamide, N,N-dimethylacetamide, quinoline, m-cresol, acetic acid and the like and mixtures thereof) yields the dihydroxy 1,4,5,8-naphthalene tetracarboxylic diimide dimer on isolation and purification.

If it is so desired to have a 1,4,5,8-naphthalene tetracarboxylic diimide dimer where $R_2$ is not equal to $R_3$ such a dimer could be synthesized as follows: A compound 2 (see FIG. 2) is dissolved in aqueous alkali which is then treated sequentially with concentrated phosphoric acid, a difunctional amine (such as 1,4-diaminobutane or 2,2-dimethyl-1,3-propane diamine) and heated to 90° C. for a period of time. Any insoluble material is filtered after which concentrated phosphoric acid is added to precipitate the product which can be collected, further purified and dried to remove residual water. Reaction of this material with an aliphatic or alicyclic hydroxyl substituted monofunctional amino compound (such as 4-aminobutane or 4-aminopentane) at elevated temperature in a suitable solvent (such as N,N-dimethylformamide, N,N-dimethylacetamide, quinoline, m-cresol, acetic acid and the like and mixtures thereof) yields a dihydroxy 1,4,5,8-naphthalene tetracarboxylic diimide dimer on isolation and purification.

Dihydroxy naphthalene tetracarboxylic diimide dimers can be prepared according to the general schemes shown in FIGS. 1-2. In embodiments, the dihydroxy dimers are prepared by the route depicted in FIG. 2. In this route, the intermediate compound 2 can be prepared at higher purity levels than a compound 1.

It will be apparent to those skilled in the art that the procedures described herein will be generally insensitive to the choice of $R_4$, $R_5$, $R_6$, $R_7$, $R_8$, $R_9$, $R_{10}$ and $R_{11}$. It will also be apparent that the introduction of $R_4$, $R_5$, $R_6$, $R_7$, $R_8$, $R_9$, $R_{10}$ and $R_{11}$ should preferentially be performed before undertaking the synthetic sequence described herein. That is, the starting materials may be changed from 1,4,5,8-naphthalene tetracarboxylic diacid (or dianhydride) to a material that already contains the desired substitution pattern. For those compounds not commercially available their synthesis would be required before undertaking the synthetic procedure described in this disclosure. The synthesis of naphthalene tetracarboxylic acids is a known process and is illustrated in the following figure (see W. Herbst and K. Hunger, "Industrial Organic Pigments" 2nd edition, VCH, 1997, p. 485):

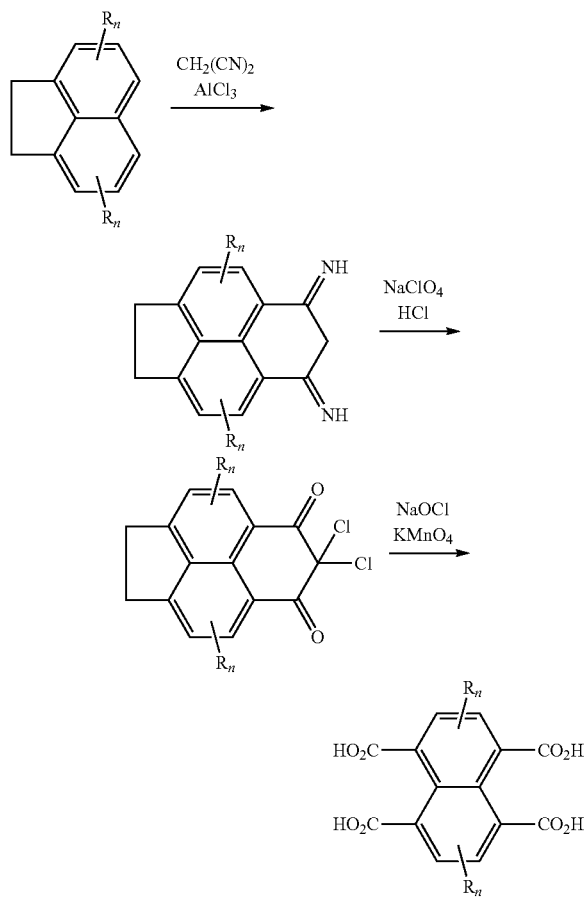

Commercially available acenaphthalene may be successively treated in separate synthetic steps with malononitrile in the presence of aluminum chloride, sodium perchlorate and hydrochloric acid and finally sodium hypochlorite and potassium permanganate. The introduction of a $R_n$ group(s) at any point in the synthesis or by starting the synthetic process from a $R_n$ substituted acenaphthalene would yield a substituted naphthalene tetracarboxylic acid. The use of such a substituted naphthalene tetracarboxylic acid for the synthesis of naphthalene tetracarboxylic acid diimide dimers as described in this development would yield compounds substituted in the $R_4$, $R_5$, $R_6$, $R_7$, $R_8$, $R_9$, $R_{10}$ and $R_{11}$ positions of the general structure illustrated in Formula I.

It should also be apparent that for certain choices and combinations of $R_4$, $R_5$, $R_6$, $R_7$, $R_8$, $R_9$, $R_{10}$ and $R_{11}$ the synthetic procedure described herein may yield structural isomers. For example, if 2-chloro-1,4,5,8-naphthalene tetracarboxylic acid was used as a starting material the chloro substituent will end up statistically distributed at the $R_4$, $R_5$, $R_6$, $R_7$, $R_8$, $R_9$, $R_{10}$ and $R_{11}$ positions.

Figure 3:
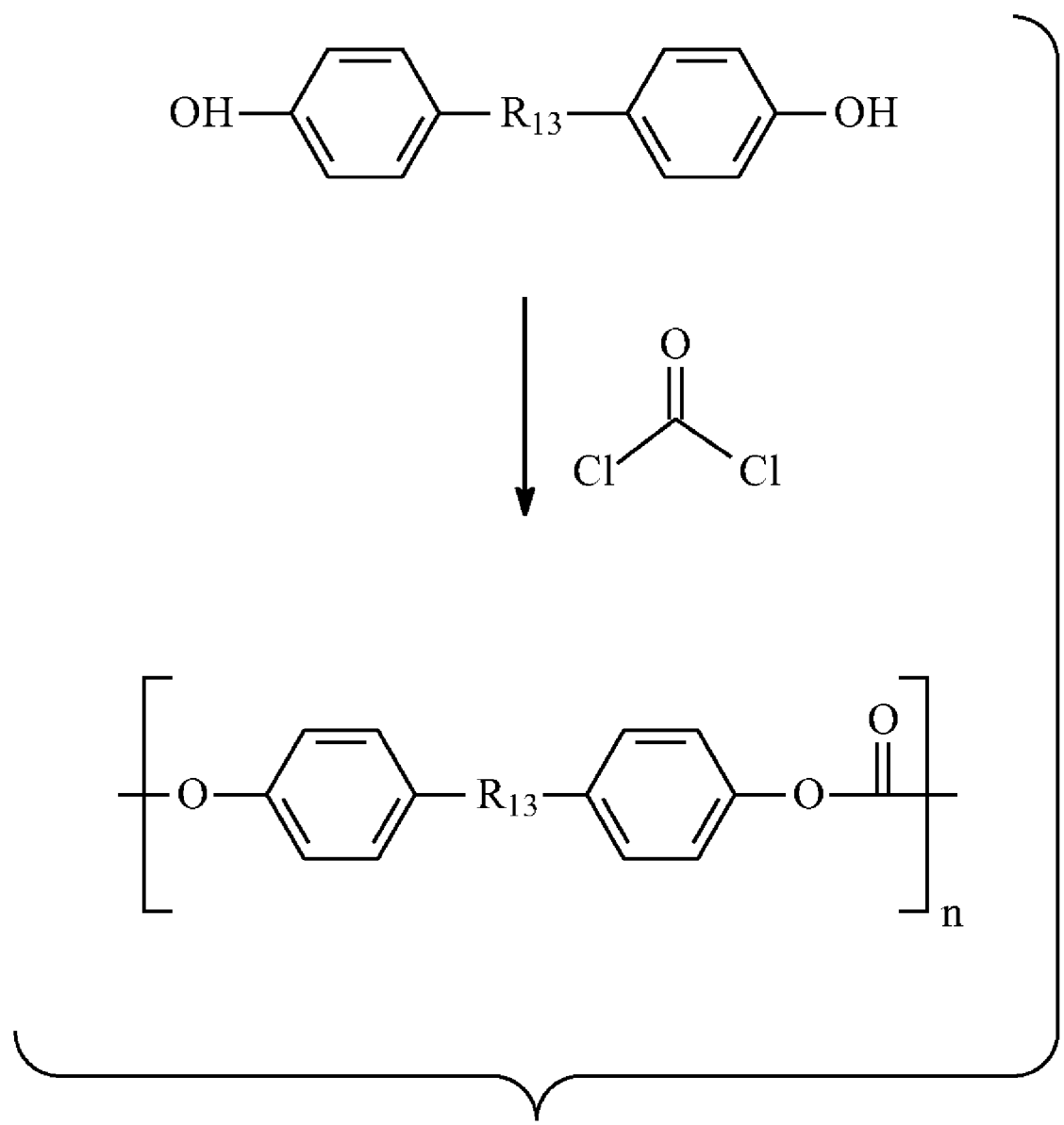
FIG. 3 depicts a first illustrative synthesis route for forming polycarbonates.
Figure 4:
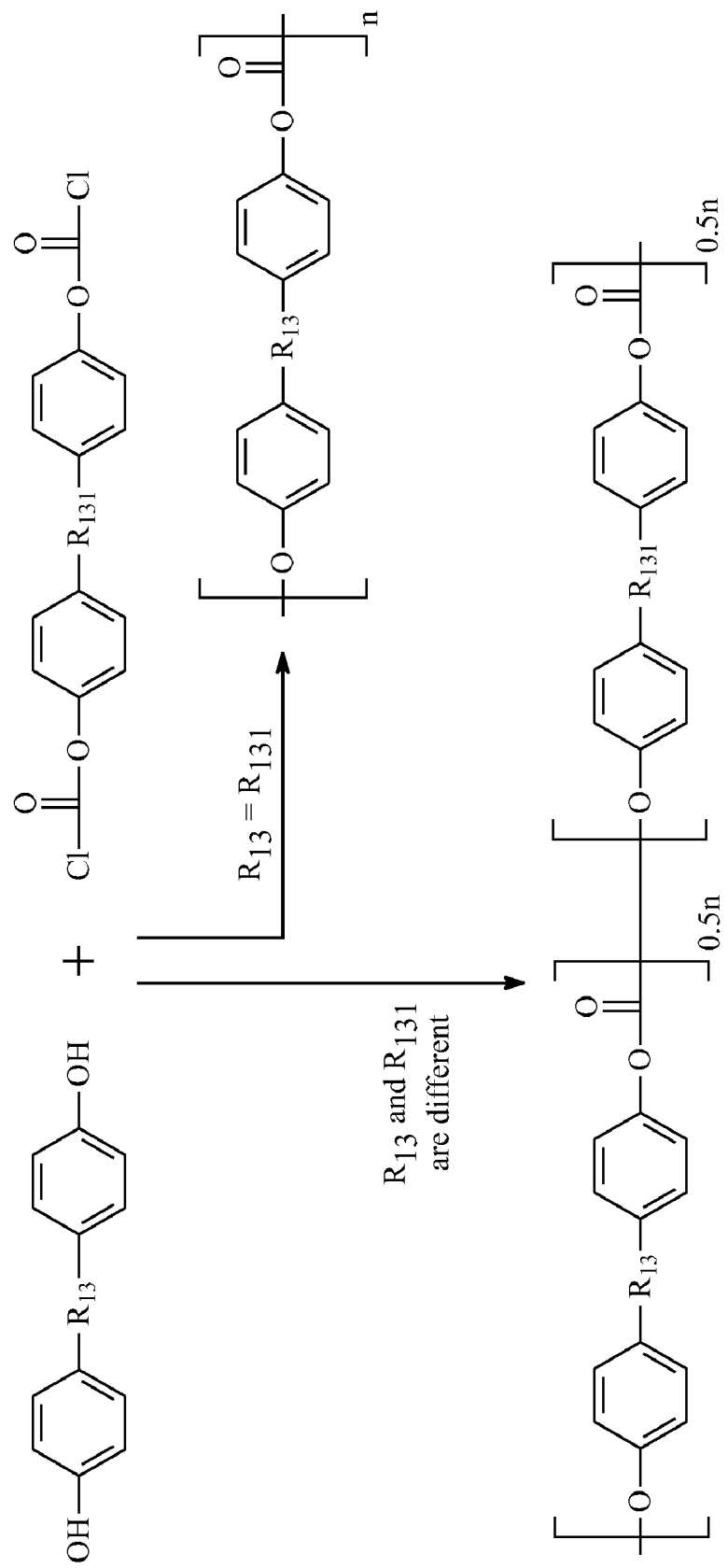
FIG. 4 depicts a second illustrative synthesis route for forming polycarbonates.
Figure 5:
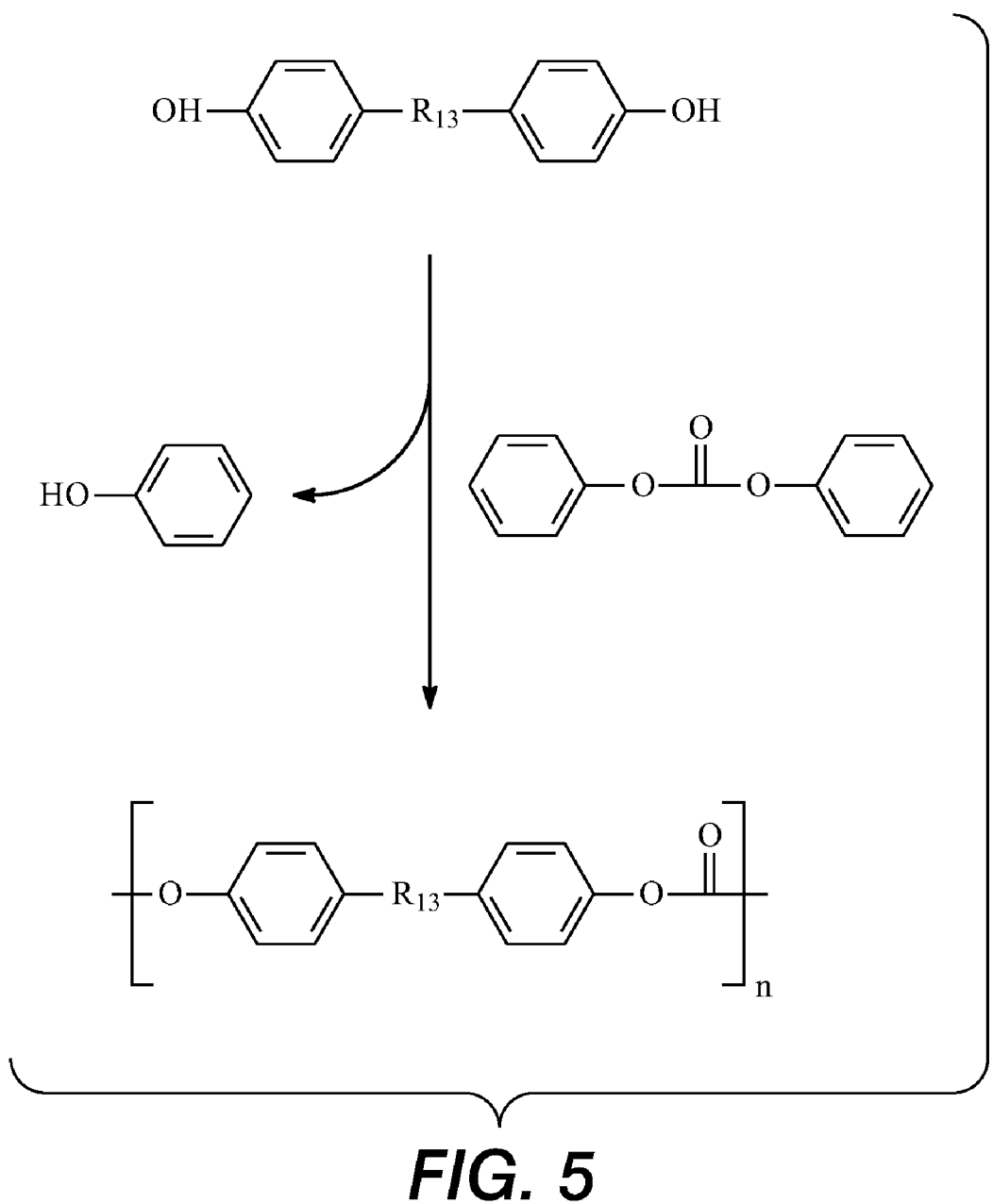
FIG. 5 depicts a third illustrative synthesis route for forming polycarbonates.

Compounds of the Formula I are generally prepared by a polycondensation reaction of the dihydroxy naphthalene tetracarboxylic diimide dimer component with an appropriate compound to yield the desired polymer. FIGS. 3-5 depict illustrative synthesis routes to prepare polycarbonate polymers. For example FIG. 3 illustrates schematically a method for the formation of a polycarbonate by reaction of a dihydroxyl compounds containing a general sub group R13 which would comprise a naphthalene tetracarboxylic acid dimer moiety, with phosgene. Such reactions are usually carried out using a two-phase reaction medium of water (usually containing a hydroxide base, such as sodium hydroxide but usually potassium hydroxide) and organic phase. An aqueous phase should be chosen in such a way as to prevent the hydrolysis of the naphthalene tetracarboxylic acid dimer moiety which is a known side reaction and would not yield the desired polymer. An organic phase should be chosen in such a way as to have the organic phase immiscible with water and so as to provide suitable solubility for the polymer produced and or the monomers if the monomers used in the process are not soluble in aqueous hydroxide base. Phosgene can either be introduced into the reaction as a gas, perhaps under pressure, or as a solution in a suitable organic solvent such as toluene. In this illustration only a homopolymer of the dihydroxyl compound containing a general sub group R13 which would comprise a naphthalene tetracarboxylic acid dimer moiety would be produced but it would be obvious to those skilled in the art that the presence of another or several other dihydroxyl compounds in the reaction medium would result in copolymers or higher copolymers respectively. In another example illustrated in FIG. 4 a polycarbonate is formed in a similar manner as above except in place of phosgene a bis-chloroformate compound (which is made by the treatment of a dihydroxyl compound with excess phosgene) is used. Reaction of a bischloroformate under similar conditions as those outlined above for the use of phosgene results in formation of a polycarbonate. If the bischloroformate used in this process is not a derivative of the same dihydroxyl compounds used then the resulting polycarbonate is a perfectly alternating polymer. It would be obvious to those skilled in the art that the presence of another or several other dihydroxyl compounds or another or several other bischloroformate compounds in the reaction medium would result in copolymers or higher copolymers respectively. In another example illustrated in FIG. 5 a polycarbonate is formed by reaction of a dihydroxyl compound containing a general sub group R13 which would comprise a naphthalene tetracarboxylic acid dimer moiety with diphenylcarbonate in a process which could be referred to as a transesterification or transcarbonylation reaction. Conditions used during such a process usually are but not limited to high reaction temperatures, Lewis acid catalyst and a mean for vacuum distillation of the produced phenol byproduct. In this illustration only a homopolymer of the dihydroxyl compound containing a general sub group R13 which would comprise a naphthalene tetracarboxylic acid dimer moiety would be produced but it would be obvious to those skilled in the art that the presence of another or several other dihydroxyl compounds in the reaction medium would result in copolymers or higher copolymers respectively. These examples are meant as illustrative examples and those skilled in the art will recognize they may not represent a complete list of the synthetic methods available for the synthesis of polycarbonates.

Figure 6:
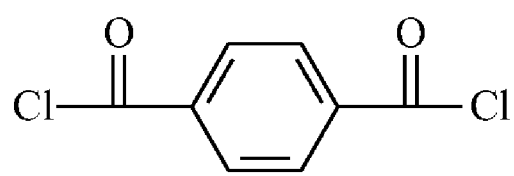
FIG. 6 depicts an illustrative synthesis route for forming polyesters.
Figure 6:
Figure 6:
Figure 6:
Figure 6:
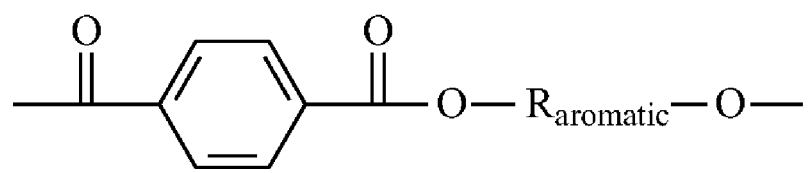
Figure 6:
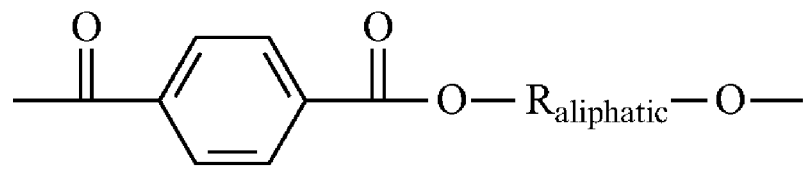

FIG. 6 depicts an illustrative synthesis route to prepare polyesters and polyesters of the present disclosure containing a naphthalene tetracarboxylic diimide dimer component. For example FIG. 6 illustrates schematically a method for the formation of a polyester by reaction of a dihydroxyl compounds containing a general sub group R15 which would or may comprise a naphthalene tetracarboxylic acid dimer moiety, with a diacid chloride compound which could optionally also have a general sub group R14 which would or may comprise a naphthalene tetracarboxylic acid dimer moiety. Such reactions are usually carried out using a two-phase reaction medium of water (usually containing a hydroxide base, such as sodium hydroxide but usually potassium hydroxide) and organic phase. An aqueous phase should be chosen in such a way as to prevent the hydrolysis of the naphthalene tetracarboxylic acid dimer moiety which is a known side reaction and would not yield the desired polymer and hydrolysis of the diacid chloride which is a known side reaction. An organic phase should be chosen in such a way as to have the organic phase immiscible with water and so as to provide suitable solubility for the polymer produced and or the monomers. The diacid chloride could be added as a solution in a suitable organic solvent such as toluene. In this illustration only a homopolymer of the dihydroxyl compound or the diacid chloride containing a general sub group R14 or R15 respectively which would or may comprise a naphthalene tetracarboxylic acid dimer moiety would be produced but it would be obvious to those skilled in the art that the presence of another or several other dihydroxyl compounds or diacid chloride compounds in the reaction medium would result in copolymers or higher copolymers respectively. In another example a polyester can be formed by reaction of a dihydroxyl compound containing a general sub group R15 which would or may comprise a naphthalene tetracarboxylic acid dimer moiety with diester compound in a process which could be referred to as a transesterification. Conditions used during such a process usually are but not limited to high reaction temperatures, Lewis acid catalyst and a mean for vacuum distillation of the produced alcohol byproduct. In this illustration only a homopolymer of the dihydroxyl compound or the diester containing a general sub group R14 or R15 respectively which would or may comprise a naphthalene tetracarboxylic acid dimer moiety would be produced but it would be obvious to those skilled in the art that the presence of another or several other dihydroxyl compounds or diester compounds in the reaction medium would result in copolymers or higher copolymers respectively. These examples are meant as illustrative examples and those skilled in the art will recognize they may not represent a complete list of the synthetic methods available for the synthesis of polycarbonates.

Figure 7:
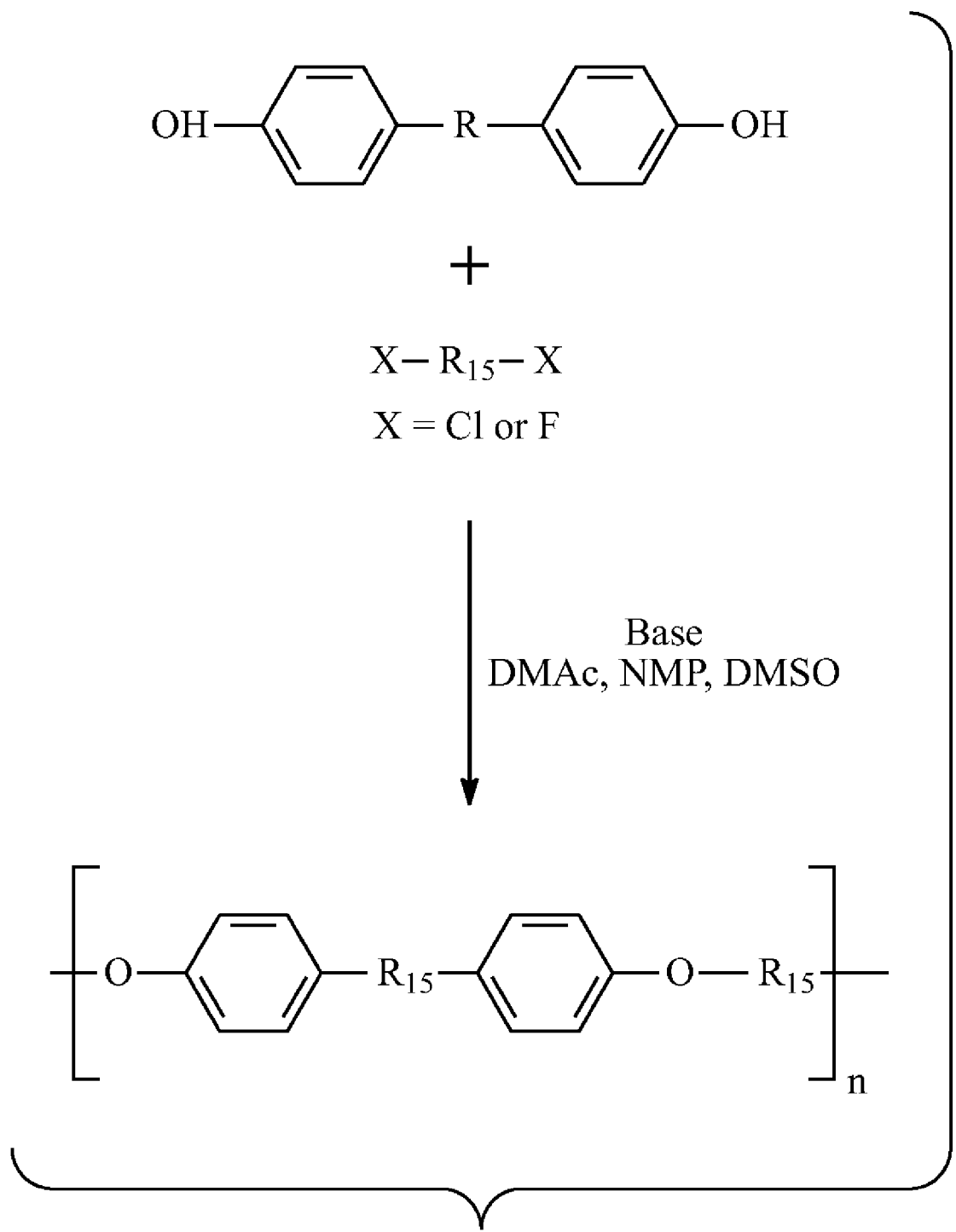
FIG. 7 depicts an illustrative synthesis route for forming polyarylyethers.

FIG. 7 depicts an illustrative synthesis route to prepare polyarylethers and polyarylethers of the present disclosure containing a naphthalene tetracarboxylic diimide dimer component. For example FIG. 7 illustrates schematically a method for the formation of a polyarylene ether by reaction of a dihydroxyl compound containing a general sub group R18 which would or may comprise a naphthalene tetracarboxylic acid dimer moiety, with a dihalo compound (where X represents a halide moiety) which is activated by an electron withdrawing group (denoted as Z) which could optionally also have a general sub group R19 which would or may comprise a naphthalene tetracarboxylic acid dimer moiety Such reactions are usually carried out in the presence of a base such as a carbonate base which could be sodium carbonate, potassium carbonate, robidium carbonate or cesium carbonate. Such reactions are usually carried out in the presence of a mixture of solvents one (such as for example toluene) to provide azeotropic removal of the water produce and one (such as a polar aprotic solvent like N,N-dimethylformamide (DMF), N,N-dimethylacetamide (DMAc), sulfolane or N-methylpyrrolidinone (NMP)) to solubilize both the monomers and polymer produced. Reaction conditions should be chosen in such a way as to produce the desired polymer without chemically damaging the naphthalene tetracarboxylic acid dimer moiety. The example is meant as illustrative example and those skilled in the art will recognize it may not represent the only synthetic method available for the synthesis of polyarylene ethers.

The polymeric materials may also be NTDI containing polymers of the Formula IX:

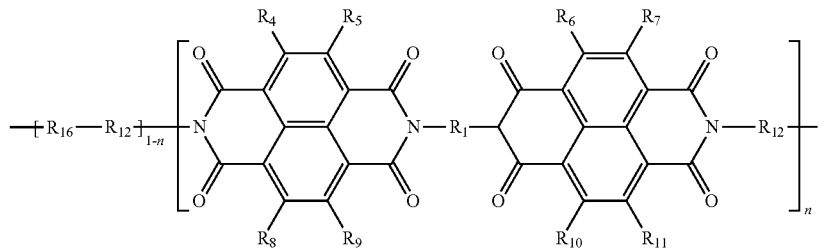

In embodiments, $R_{12}$ is independently selected from the group consisting of a hetero atom containing group or a hydrocarbon group that is optionally substituted at least once with a hetero atom moiety; In embodiments, $R_{16}$ is selected from

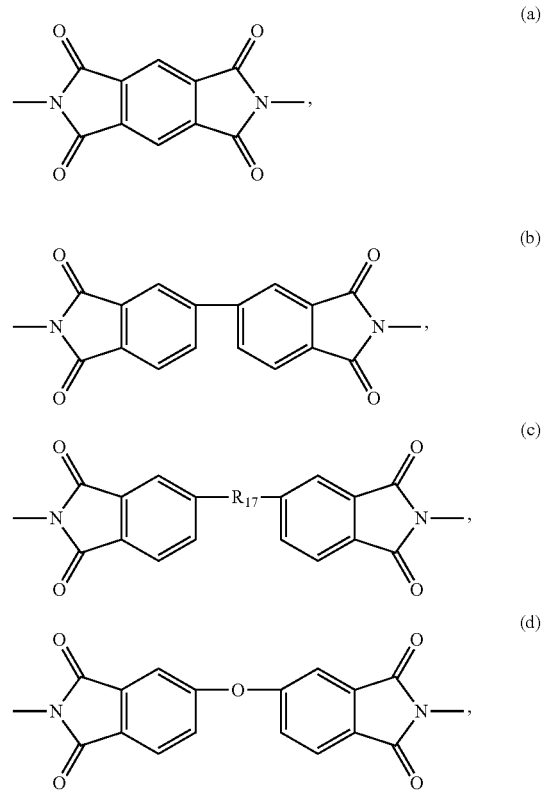

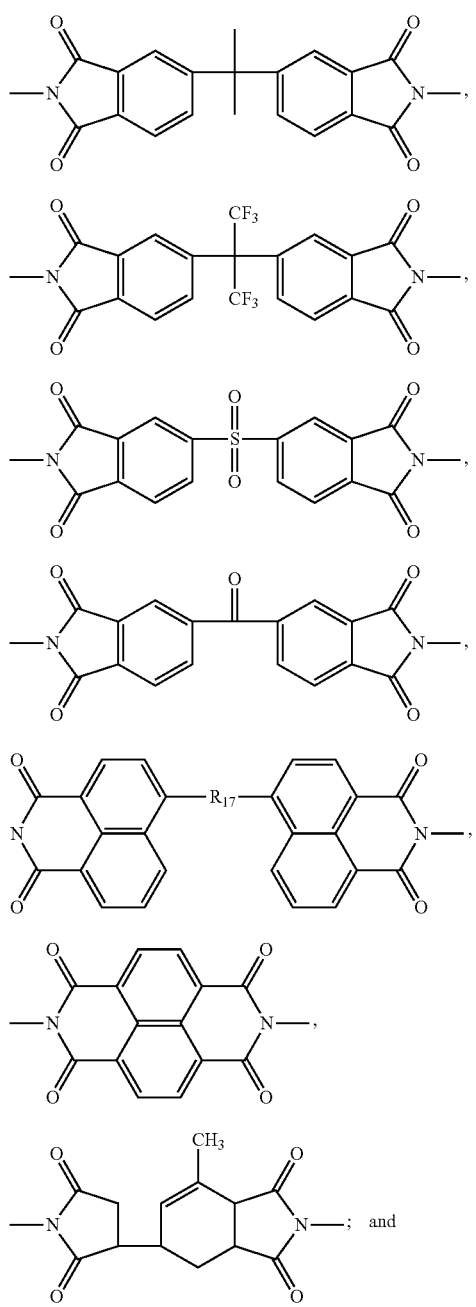

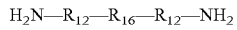

wherein $R_{20}$ may be independently selected from the group consisting of a hetero atom containing group or a hydrocarbon group that is optionally substituted at least once with a hetero atom moiety; The $R_{12}$—$R_{16}$—$R_{12}$ portion of the polymer of Formula IX is also considered and referred to herein as a binder or resin component of the polymer comprising an NTDI dimer.

Figure 8:
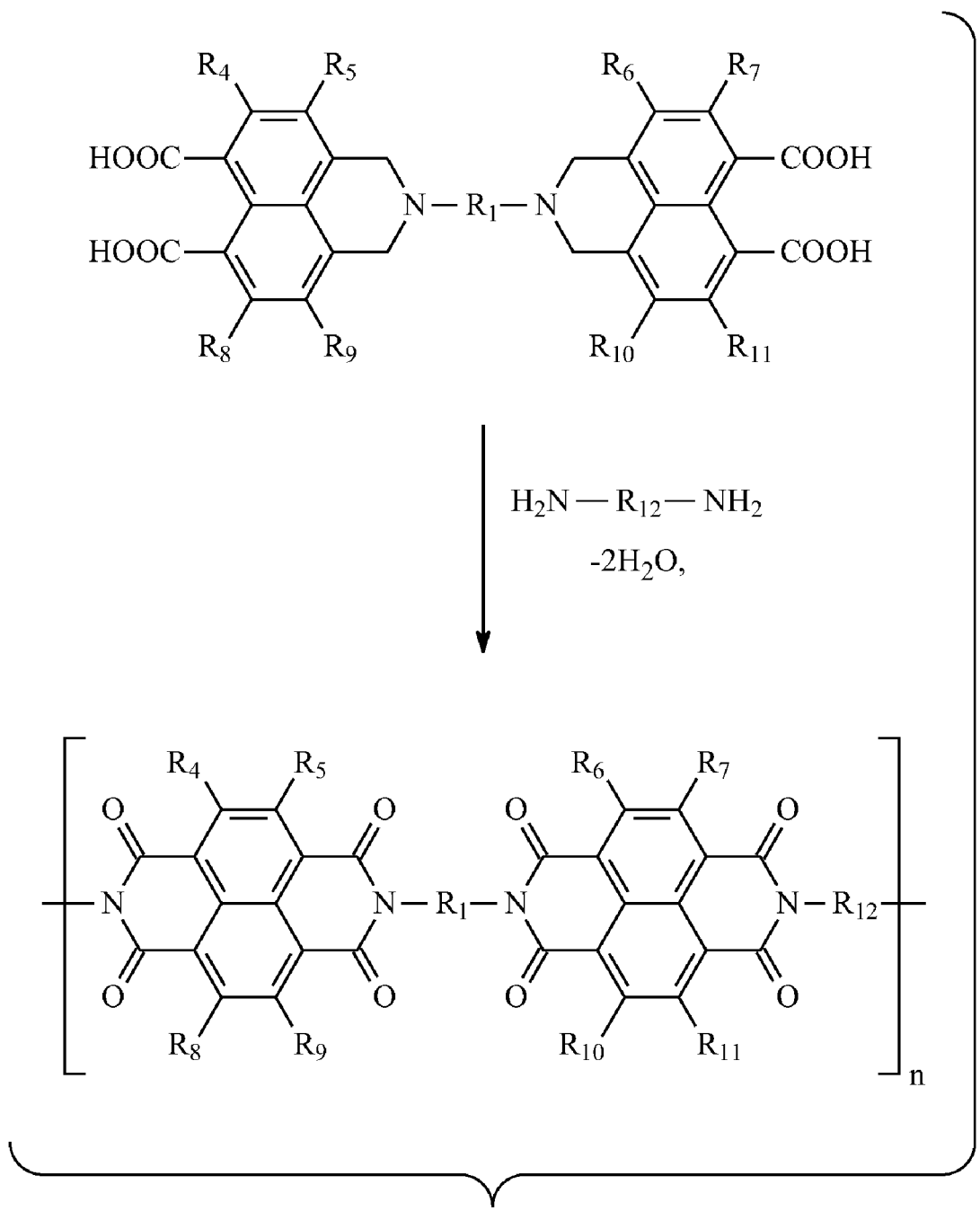
FIG. 8 depicts an illustrative synthesis route for forming a hybrid binder/electron-transporting polyimide containing a naphthalene tetracarboxylic diimide dimer.

FIG. 8 depicts an illustrative synthesis route to prepare naphthalene tetracarboxylic diimide dimer polymides of Formula IX. As shown in FIG. 8, a polyimide may be made by polycondensation of a compound of type 2, which may be formed as shown in FIG. 2, and a desired diamino compound. Suitable diamino compounds include compounds of the formula:

$$H_2N-R_{12}-R_{16}-R_{12}-NH_2$$

wherein $R_{12}$ may be independently selected from the group consisting of a hetero atom containing group or a hydrocarbon group that is optionally substituted at least once with a hetero atom moiety; and $R_{16}$ is selected from:

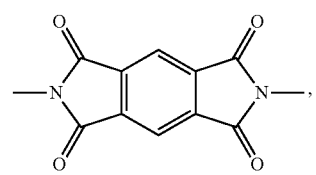
(a)

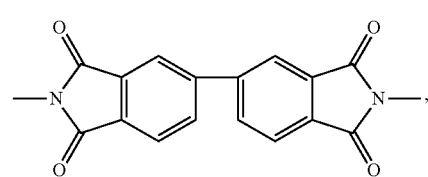
(b)

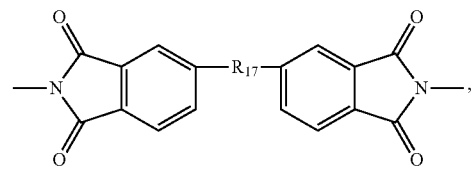
(c)

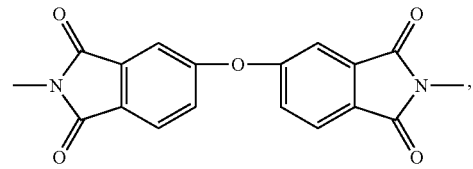
(d)

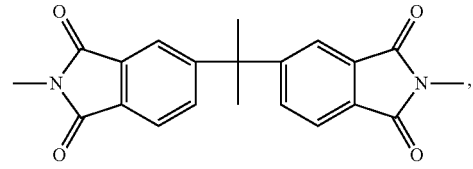
(e)

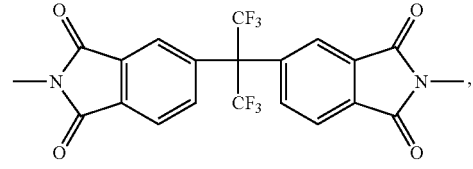
(f)

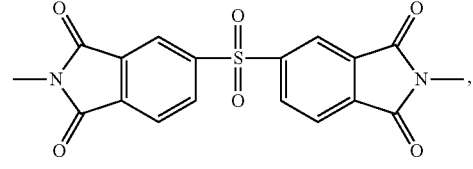
(g)

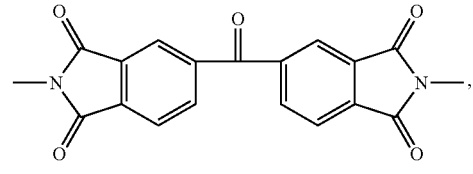
(h)

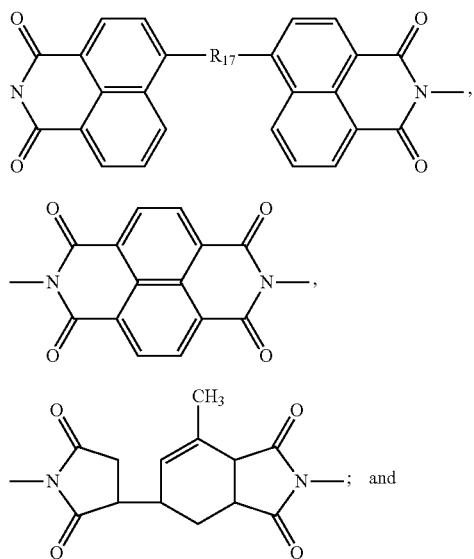

wherein $R_{20}$ may be independently selected from the group consisting of a hetero atom containing group and a hydrocarbon group that is optionally substituted at least once with a hetero atom moiety. The $R_{12}$—$R_{16}$—$R_{12}$ portion of the polymer of Formula IX is also considered and referred to herein as a binder or resin component of the polymer comprising an NTDI dimer. The reaction is generally carried out in a solution of the components, i.e., a solution of compound 2 and the diamino compound, in a polar aprotic solvent such as DMAC, NMP, DMF, and the like or a phenolic solvent such as m-cresol and the like. The reaction is generally carried out at temperatures greater than about 200° C. and may require the presence of a catalyst which is typically isoquinoline or the like and present in quantities of no more than 10 mole percent.

The NTDI dimer component is present in an amount of about 1 to about 85 percent by weight of the polymer, while the binder or resin component is present in an amount of about 99 to about 15 percent by weight of the polymer.

In embodiments, the NTDI dimmer component comprises about 20 to about 50 percent by weight of the polymer, and the binder or resin component comprises about 80 to about 50 percent by weight of the polymer.

Polymeric materials comprising NTDI dimers, such as, for example, compounds of Formulas I and IX are suitable for use in an active layer or an electrophotographic element in an imaging member. Reference to compounds of Formula I also includes those polymers of Formulas VI, VII, and VIII. The compounds of Formulas I and IX exhibit dual functionality with respect to their use in an imaging member. Specifically, the compounds of Formulas I and IX are capable of function as a binder and an electron-transporting material. The dual functionality stems from the fact that the compounds are polymeric materials such as, for example, polycarbonates, polyesters, polyarylethers, and polyimides, that include an electron-transporting moiety in the naphthalene tetracarboxylic diimide dimer component. The compounds of Formulas I and IX are suitable for use in both multi-layer and single layer photoreceptors.

The photoconductor elements of the disclosure can have any known configuration. The photoconductor elements can have one active layer comprising both a charge generation material and an electron-transport agent of Formula I or Formula IX, or they can be multiactive elements.

In embodiments, the photoconductive elements include a single active layer. The single active layer comprises a charge generating material, a hole transporting material, and a dual functional binder/electron-transporting material of Formula I (including materials of Formula VI, VII, and VIII), Formula IX or combinations thereof. In embodiments, the charge generation material is present in an amount of from about 5 to about 35 percent by weight, the hole transporting material is present in an amount of from about 30 to about 65 percent by weight, and the dual functional binder/electron-transporting material, i.e., the polymer containing the NTDI dimer, is present in an amount of from about 65 to about 10 weight percent of the single active layer composition.

Any material suitable as a charge generating material may be used in a single active layer photoconductive element. Non-limiting examples of suitable charge generating materials are described herein. Any material suitable as a hole-transporting material may be used in a single active layer photoconductor element according to the present disclosure. Non-limiting examples of suitable hole-transporting materials or agents are described herein.

Further, additional electron-transporting materials may be added to the single active layer photoconductor element of the disclosure. Non-limiting examples of suitable electron-transport materials are described herein. When additional electron-transporting materials are employed, the additional electron-transporting material is present in an amount of from about 5 to about 45 percent by weight.

A single active layer of the present disclosure is generally formed by preparing a particle dispersion with the hole transporting material and optionally the additional electron-transporting material(s) present in a solid state solution within the polymer materials comprising a naphthalene tetracarboxylic diimide dimer, i.e., the materials of Formula I (including materials of Formula VI, VII, and VIII) and/or Formula IX. The dispersion may be formed into a single layer photoreceptor by any suitable method.

In other embodiments, the photoconductive element is a multiactive element. The multiactive elements have at least one charge generation layer having at least one charge generation material and one charge transport layer having at least one charge transport agent of Formula I or Formula IX. In addition to charge generation layers and charge transport layers, the photoconductor elements of this disclosure may include electrically conductive layers and optional additional layers, such as subbing layers, adhesive layers, abrasion resistant layers, and electronic charge barrier layers which are all well known in the art.

In embodiments, the photoconductor elements of this disclosure have dimensional stability. This can be accomplished by using an electrically conductive layer that is itself dimensionally stable, or by forming the element on a dimensionally stable conductive substrate. A dimensionally stable electrically conductive layer or the combination of an electrically conductive layer and a dimensionally stable substrate will be referred to as an electrically conductive support. A dimensionally stable substrate may be thermally stable and may be electrically insulating. Conventional dimensionally stable substrates such as films and sheets of polymeric materials may be used. Examples of polymers used in films include cellulose acetate, polycarbonates, polyesters, such as poly (ethylene terephthalate) and poly(ethylene naphthalate), and polyimides. Typical film substrates have a thickness in the range of about 100 to 200 microns, although thicker and thinner layers can be employed.

The charge transport layer having at least one polymer comprising a naphthalene tetracarboxylic diimide dimer such as a polymer of, for example, Formula I or Formula IX can be the top layer of the photoconductor element through which the light or activating energy passes to the charge generation layer, because the compounds of Formula I and Formula IX are substantially transparent to visible and near infrared region light. There will be little or no loss in incident light as such light passes through a charge transport layer of an imaging layer in accordance with the disclosure. When the charge transport layer is the top layer, it provides the additional benefit of protecting the charge generation layer from abrasion caused when paper, cleaning brushes, or the like, contact the photoconductor element. These photoconductor elements are particularly useful as positively-charged photoconductor elements.

Photoconductor elements that include a compound of, for example, Formula I or Formula IX as the electron-transport agent display photosensitivity in the spectral range of for example about 400 to about 900 nm. The exact photosensitivity achieved in any given photoconductor element is dependent upon the choice of charge generation material(s), and the configuration of layer(s) in the photoconductor element. The term "photosensitivity" as used herein means the capacity of a photoconductor element to decrease in surface potential upon exposure to actinic radiation. For purposes of the present disclosure, photosensitivity is conveniently measured by corona charging the element to a certain potential, exposing the charged element to a monochromatic light and measuring the decrease of the surface potential. The amount of light necessary to discharge the element to a certain potential is defined as the "exposure requirement" for that potential. The exposure requirement to discharge the photoconductor element to half of its initial value is denoted $E_{0.5}$.

The photoconductor elements can employ various electrically conductive layers. For example, the conductive layer can be a metal foil which is laminated to the substrate. Suitable metal foils include those comprised of aluminum, zinc, copper, and the like. Alternatively, vacuum deposited metal layers upon a substrate are suitable. Examples of suitable vapor deposited metal include, but are not limited to vapor deposited silver, nickel, gold, aluminum, chromium, and metal alloys. The thickness of a vapor deposited metal layer can be in the range of about 20 to about 500 angstroms. Conductive layers can also comprise a particulate or dissolved organic or inorganic conductor or semiconductor distributed in a binder resin. For example, a conductive layer can comprise compositions of protective inorganic oxide and about 30 to about 70 weight percent of conductive metal particles, such as a vapor deposited conductive cermet layer as described in U.S. Pat. No. 3,880,657. Also see in this connection the teachings of U.S. Pat. No. 3,245,833 relating to conductive layers employed with barrier layers. Organic conductive layers can be employed, such as those comprised of a sodium salt of a carboxyester lactone of maleic anhydride in a vinyl acetate polymer, as taught, for example, in U.S. Pat. Nos. 3,007,901 and 3,262,807. The substrate and the conductive layer can also be formulated as a consolidated layer which can be a metal plate or drum. For example, suitable plates or drums can be formed of metals such as aluminum, copper, zinc, brass and steel.

In the photoconductor elements of the disclosure, the conductive layer is optionally overcoated by a barrier adhesive or subbing layer. The barrier layer typically has a dry thickness in the range of about 0.01 to about 5 microns. Typical subbing layers are solvent soluble, film-forming polymers, such as, for example, cellulose nitrate, nylon, polyesters, copolymers of poly(vinyl pyrrolidone) and vinylacetate, and various vinylidene chloride-containing polymers. Preferred subbing layers are comprised of nylon, and polyacrylic and methacrylic esters. The barrier layer coating composition can also contain minor amounts of various optional additives, such as surfactants, levelers, plasticizers, and the like.

Any convenient method may be used for the application of a subbing layer. In embodiments, the subbing layer is formed by dissolving the polymer in a solvent, and then coating the solution over the conductive layer.

In embodiments, the solvents are volatile, that is evaporable, at temperatures below about 150° C. Examples of suitable solvents include petroleum ethers; aromatic hydrocarbons, such as benzene, toluene, xylene, and mesitylene; ketones, such as acetone, and 2-butanone; ethers, such as tetrahydrofuran and diethyl ether; alkanols, such as isopropyl alcohol; and halogenated aliphatic hydrocarbons, such as methylene chloride, chloroform, and ethylene chloride. Coating solvents include for example chlorinated aliphatic hydrocarbons. A nylon subbing layer may be coated from an alcohol. Mixtures of different solvents or liquids can also be employed.

The barrier layer coating composition is applied by using a technique such as knife coating, spray coating, spin coating, extrusion hopper coating, curtain coating, or the like. After application, the coating composition is conveniently air dried.

In addition to organic polymers, inorganic materials can be utilized for the formation of barrier layers. Silicon dioxide, for example, can be applied to a conductive support by vacuum deposition.

The charge generation layer is applied over the conductive layer, or over the barrier layer, if a barrier layer is employed.

The charge generating (or generation) layer is conveniently comprised of at least one conventional charge generation material that is typically dispersed in a polymeric binder. The layer can have a thickness that varies over a wide range, typical layer thicknesses being in the range of about 0.05 to about 5 microns. As those skilled in the art will appreciate, as layer thickness increases, a greater proportion of incident radiation is absorbed by a layer, but the likelihood increases of trapping a charge carrier which then does not contribute to image formation. Thus, an optimum thickness of a layer can constitute a balance between these competing influences.

Charge generation materials comprise materials that are capable of generating electron/hole pairs upon exposure to actinic radiation in the presence of an electric field and transferring the electrons to an electron-transport agent. The charge generation material is present in a polymeric binder or is present as a separate solid phase. The process by which electron/hole pairs are generated may require the presence of an electron-transport agent. Suitable charge generation materials may be, in embodiments, substantially incapable of generating and/or transferring electrons/hole pairs to an electron-transport agent in the absence of actinic radiation.

A wide variety of materials known in the art as charge generation materials can be employed including inorganic and organic compounds. Suitable inorganic compounds include, for example, zinc oxide, lead oxide, and selenium. Suitable organic materials include various particulate organic pigment materials, such as phthalocyanine pigments, and a wide variety of soluble organic compounds including metallo-organic and polymeric organic charge generation materials. A partial listing of representative materials may be found, for example, in Research Disclosure, Vol. 109, May, 1973, page 61, in an article entitled "Electrophotographic Elements, Materials and Processes", at paragraph IV(A)

thereof. This partial listing of well-known charge generation materials is hereby incorporated by reference.

Examples of suitable organic charge generation materials include phthalocyanine pigments such as a bromoindium phthalocyanine pigment described in U.S. Pat. Nos. 4,666,802 and 4,727,139, or a titanylphthalocyanine pigment such as a titanyl tetrafluoropthalocyanine described in U.S. Pat. No. 4,701,396; various pyrylium dye salts, such as pyrylium, bispyrylium, thiapyrylium, and selenapyrylium dye salts, as disclosed, for example, in U.S. Pat. No. 3,250,615; fluorenes, such as 7,12-dioxo-13-dibenzo(a,h) fluorene, and the like; aromatic nitro compounds of the kind disclosed in U.S. Pat. No. 2,610,120; anthrones such as those disclosed in U.S. Pat. No. 2,670,284; quinones such as those disclosed in U.S. Pat. No. 2,670,286; thiazoles, such as those disclosed in U.S. Pat. No. 3,732,301; various dyes such as cyanine (including carbocyanine), merocyanine, triarylmethane, thiazine, azine, oxazine, xanthene, phthalein, acridine, azo, anthraquinone dyes, and the like, and mixtures thereof.

The charge generation material, or a mixture of charge generation materials, is usually applied from a solution or dispersion in a coating composition to form a charge generating layer in an element over a barrier layer of the type described herein. Also typically present as dissolved solids in a charge generation layer coating composition are a binder polymer and optional additives, such as surfactants, levelers, plasticizers, sensitizers, and the like. The solids comprising a charge generation layer on a 100 weight percent total basis typically comprise 1 to about 70 weight percent of charge-generation material, 0 to about 99 weight percent of polymeric binder, and 0 to about 50 weight percent of total additives. In embodiments, the coating composition contains from about 6 to about 15 weight percent of solids, the balance being solvent. Suitable solvents are those identified above in relation to the barrier layer. In embodiments, additives for a composition to be coated to form a charge generation layer are charge transport agents and surfactants.

Any hydrophobic organic polymer known to the photoconductor element art as a binder can be used for the polymeric binder in the charge generating layer. These polymers are film forming and are preferably organic solvent soluble, and, in solid form, display high dielectric strength and electrical insulating properties. Suitable polymers include, for example, styrene-butadiene copolymers; polyvinyl toluene-styrene copolymers; silicone resins, styrene alkyd resins, silicone-alkyd resins; soya-alkyd resins; poly(vinyl chloride); poly(vinylidene chloride); vinylidene chloride-acrylonitrile copolymers; poly(vinyl acetate); vinyl acetate-vinyl chloride copolymers; poly(vinyl acetate); vinyl acetate-vinyl chloride copolymers; poly(vinyl acetals), such as poly(vinyl butyral); polyacrylic and methacrylic esters, such as poly(methyl methacrylate), poly(n-butyl methacrylate), poly(isobutyl methacrylate), etc.; polystyrene, nitrated polystyrene; polymethylstyrene; isobutylene polymers; polyesters, such as poly[4,4'-(2-norbornylidene)bisphenylene azelate-co-terephthalate(60/40)], and poly[ethylene-co-alkylene-bis(alkylene-oxyaryl)-phenylenedicarboxylate]; phenolformaldehyde resins; ketone resins; polyamides; polycarbonates; polythiocarbonates; poly[ethylene-co-isopropylidene-2,2-bis(ethyleneoxyphenylene)terephthalate]; copolymers of vinyl haloarylates and vinyl acetate, such as poly(vinyl-m-bromobenzoate-co-vinyl acetate); chlorinated polyolefins such as chlorinated polyethylene; and the like. In embodiments, polymers may be either polyesters or polycarbonates.

One or more charge transport agents can be added to a charge generation layer coating composition, such as 1,1-bis(4-di-p-tolylaminophenyl)cyclohexane, as taught in U.S. Pat. No. 4,127,412, tri-p-tolylamine, and the like or, electron-transport agents, such as compounds of Formula I or Formula IX, or any other electron-transport agents known to the art. Coating aids, such as levelers, surfactants, cross linking agents, colorants, plasticizers, and the like, can also be added. The quantity of each of the respective additives present in a coating composition can vary, depending upon results desired and user preferences.

A charge generating layer composition is applied by coating the composition over the barrier layer using a technique such as above described for coating a barrier layer composition. After coating, the charge generating layer composition is usually air dried.

Instead of a charge generation material being dispersed in a polymeric binder, a charge generation layer can, in some cases, depending upon the charge generation material involved, be comprised substantially entirely of only such a material. For example, a perylene dicarboximide pigment of the Formula in column 11, line 45, of U.S. Pat. No. 5,468,583, wherein R is an aryl or arylalkylenyl group, can be applied over an electrically conductive layer under vacuum by sublimation, such as under subatmospheric pressures of about $10^{-2}$ to about $10^{-5}$ mm Hg at temperatures in the range of about 200° C. to about 400° C.

An illustrative charge generation material comprises titanylphthalocyanine or titanyl tetrafluorophthalocyanine pigment described in U.S. Pat. No. 4,701,396, the disclosure of which is incorporated herein by reference. An illustrative binder in the charge generating layer is poly[4,4'-(2-norbornylidene)bisphenylene azelate-co-terephthalate(60/40)].

The charge transport layer is applied over the charge generation layer. When the charge transport layer contains at least one compound of Formula I and Formula IX, an electron-transporting charge transport layer is produced.

A charge transport layer, if desired, can contain, in addition to at least one compound of Formula I and Formula IX, at least one additional electron-transport agent of a type known to the art. Suitable electron-transport agents include, but are not limited to, 2,4,7-trinitro-9-fluorenone, substituted 4-dicyanomethylene-4H-thiopyran 1,1-dioxides, and substituted anthraquinone biscyanoimines.

The charge transport layer comprises at least one of the compounds of Formula I (including the compounds of Formula VI, VII, and VIII) and/or Formula IX. As previously described herein, the compounds of Formula I and Formula IX are capable of functioning as both a binder and an electron-transporting material. Thus, in embodiments, the charge transport layer may include 100 weight percent of a compound of Formula I or Formula IX or a combination of compounds of Formula I and Formula IX. In other embodiments, the charge transport layer may include one or more additional electron-transporting materials. In embodiments, the charge transport layer may comprise from about 30 to about 90 percent by weight of a compound or material of Formula I, or Formula IX, or combinations thereof, and from about 10 to about 70 percent by weight of an electron-transporting material (other than the compounds of Formulas I and IX).

The thickness of the charge transport material is not limited, other than by size constraints. Typically, a charge transport layer has a thickness in the range of about 10 to about 25 microns, although thicker and thinner layers can be employed.

A charge transport layer can be produced in a bipolar form, if desired, by additionally incorporating into the layer at least one hole transport agent. Such an agent preferentially accepts and transports positive charges (holes). If employed, the quantity of hole transport agent(s) present in a charge transport layer on a total layer weight basis may be in the range of about 10 to about 50 weight percent, although larger and smaller quantities can be employed.

Examples of suitable organic hole transport agents known to the prior art include, but are not limited to carbazoles, arylamines, polyarylalkanes, strong lewis bases, and hydrazones.

Suitable carbazoles include, but are not limited to, carbazole, N-ethyl carbazole, N-isopropyl carbazole, N-phenyl carbazole, halogenated carbazoles, various polymeric carbazole materials such as poly(vinyl carbazole), halogenated poly(vinyl carbazole), and the like.

Suitable arylamines include, but are not limited to monoarylamines, diarylamines, triarylamines and polymeric arylamines. Specific arylamine organic photoconductors include the nonpolymeric triphenylamines illustrated in U.S. Pat. No. 3,180,730; the polymeric triarylamines described in U.S. Pat. No. 3,240,597; the triarylamines having at least one of the aryl radicals substituted by either a vinyl radical or a vinylene radical having at least one active hydrogen-containing group, as described in U.S. Pat. No. 3,567,450; the triarylamines in which at least one of the aryl radicals is substituted by an active hydrogen-containing group, as described by U.S. Pat. No. 3,658,520; and tritolylamine.

Suitable polyarylalkanes, include, but are not limited, to those of the type described in U.S. Pat. Nos. 3,274,000; 3,542,547; 3,625,402; and 4,127,412.

Examples of suitable strong Lewis bases, such as aromatic compounds, including aromatically unsaturated heterocyclic compounds free from strong electron-withdrawing groups. Examples include tetraphenylpyrene, 1-methylpyrene, perylene, chrysene, anthracene, tetraphene, 2-phenylnaphthalene, azapyrene, fluorene, fluorenone, 1-ethylpyrene, acetyl pyrene, 2,3-benzochrysene, 3,4-benzopyrene, 1,4-bromopyrene, phenylindole, polyvinyl carbazole, polyvinyl pyrene, polyvinyltetracene, polyvinyl perylene and polyvinyl tetraphene.

Suitable hydrazones include, but are not limited to the dialkyl-substituted aminobenzaldehyde-(diphenylhydrazones) of U.S. Pat. No. 4,150,987; alkylhydrazones and arylhydrazones as described in U.S. Pat. Nos. 4,554,231; 4,487,824; 4,481,271; 4,456,671; 4,446,217; and 4,423,129, which are illustrative of the hydrazone hole transport agents.

Other useful hole transport agents are described in Research Disclosure, Vol. 109, May, 1973, pages 61-67 paragraph IV(A)(2) through (13).

One or more other electron-transporting agents may be used with the present multi-functional or hybrid polymers comprising naphthalene tetracarboxylic diimide dimers in photoconductor elements and other electronic devices. Examples of such other electron-transporting agents include:

a) carboxylfluorenone malonitrile (CFM) derivatives represented by the general structure:

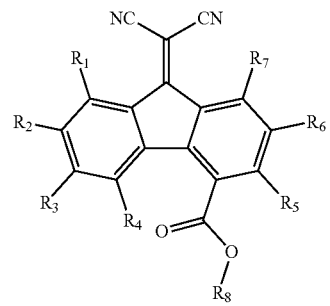

wherein each R is independently selected from the group consisting of hydrogen, alkyl having 1 to 40 carbon atoms, alkoxy having 1 to 40 carbon atoms, phenyl, substituted phenyl, higher aromatic such as naphthalene and anthracene, alkylphenyl having 6 to 40 carbon atoms, alkoxyphenyl having 6 to 40 carbon atoms, aryl having 6 to 30 carbon atoms, substituted aryl having 6 to 30 carbon atoms and halogen; b) a nitrated fluorenone derivative represented by the general structure:

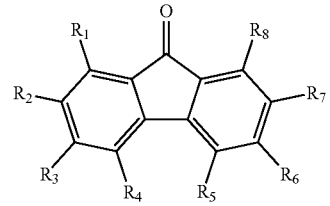

wherein each R is independently selected from the group consisting of hydrogen, alkyl having 1 to 40 carbon atoms, alkoxy having 1 to 40 carbon atoms, phenyl, substituted phenyl, higher aromatic such as naphthalene and anthracene, alkylphenyl having 6 to 40 carbon atoms, alkoxyphenyl having 6 to 40 carbon atoms, aryl having 6 to 30 carbon atoms, substituted aryl having 6 to 30 carbon atoms and halogen, and at least 2 R groups are chosen to be nitro groups; c) a 1,1'-dioxo-2-(aryl)-6-phenyl-4-(dicyanomethylidene)thiopyran derivative represented by the general structure:

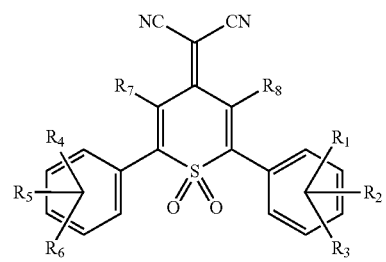

wherein each R is independently selected from the group consisting of hydrogen, alkyl having 1 to 40 carbon atoms, alkoxy having 1 to 40 carbon atoms, phenyl, substituted phenyl, higher aromatic such as naphthalene and anthracene, alkylphenyl having 6 to 40 carbon atoms, alkoxyphenyl having 6 to 40 carbon atoms, aryl having 6 to 30 carbon atoms, substituted aryl having 6 to 30 carbon atoms and halogen; d) A carboxybenzylnaphthaquinone derivative represented by the following general structure:

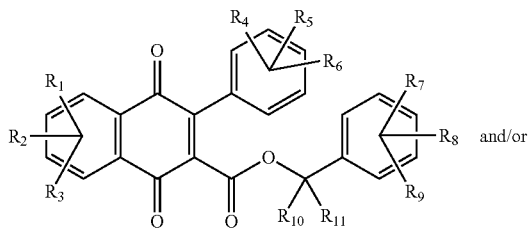

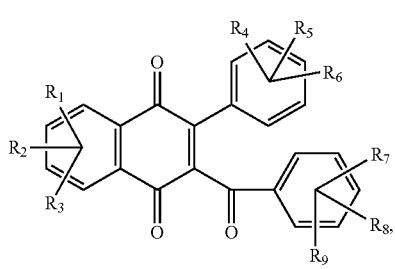

wherein each R is independently selected from the group consisting of hydrogen, alkyl having 1 to 40 carbon atoms, alkoxy having 1 to 40 carbon atoms, phenyl, substituted phenyl, higher aromatic such as naphthalene and anthracene, alkylphenyl having 6 to 40 carbon atoms, alkoxyphenyl having 6 to 40 carbon atoms, aryl having 6 to 30 carbon atoms, substituted aryl having 6 to 30 carbon atoms and halogen; e) a diphenoquinone represented by the following general structure:

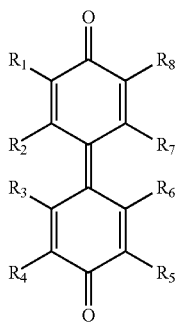

and mixtures thereof, wherein each R is independently selected from the group consisting of hydrogen, alkyl having 1 to 40 carbon atoms, alkoxy having 1 to 40 carbon atoms, phenyl, substituted phenyl, higher aromatic such as naphthalene and anthracene, alkylphenyl having 6 to 40 carbon atoms, alkoxyphenyl having 6 to 40 carbon atoms, aryl having 6 to 30 carbon atoms, substituted aryl having 6 to 30 carbon atoms and halogen.

Additionally, another suitable electron-transporting agent includes a naphthalene tetracarboxylic diimide dimer as described in U.S. application Ser. No. 10/197,933, published as U.S. Patent Application Publication No. 2004/0013959.

In addition to an electron-transport agent of Formula I or Formula IX, and optionally additional charge transport agent(s) and a binder polymer, the charge transport layers in the photoconductor elements of this disclosure may contain various optional additives, such as surfactants, levelers, plasticizers, and the like. On a 100 weight percent total solids basis, a charge transport layer can contain for example up to about 15 weight percent of such additives, although it may contain less than about 1 weight percent of such additives.

In embodiments, the charge transport layer solid components are conveniently preliminarily dissolved in a solvent to produce a charge transport layer composition containing for example about 8 to about 20 weight percent solids with the balance up to 100 weight percent being the solvent. The solvents used can be those hereinabove described.

Coating of the charge transport layer composition over the charge generation layer can be accomplished using a solution coating technique such as knife coating, spray coating, spin coating, extrusion hopper coating, curtain coating, and the like. After coating, the charge transport layer composition is usually air dried.

A charge transport layer can be formed of two or more successive layers each of which has the same or different total solids composition. In such event at least one charge transport sublayer contains at least one compound of Formula I or Formula IX.

Photoconductor elements of this disclosure may display dark decay values of for example no more than about 20 V/sec, or no more than about 5 V/sec. The term "dark decay" as used herein means the loss of electric charge and consequently, electrostatic surface potential from a charged photoconductor element in the absence of activating radiation.

For present purposes of measuring dark decay, a single-active-layer photoconductive element or a multilayered photoconductor element is charged by use of a corona discharge device to a surface potential in the range of about +300 to about +600 volts. Thereafter, the rate of charge dissipation and decrease of surface potential in volts per second is measured. The element is preliminarily dark adapted and maintained in the dark without activating radiation during the evaluation using ambient conditions of temperature and pressure.

Suitable photoconductor elements display reusability, that is, the ability to undergo repeated cycles of charging and discharging without substantial alteration of their electrical properties.

Those skilled in the art will appreciate that other variations in the structure of photoconductor elements incorporating a compound of Formula I or Formula IX are possible and practical. For example, various different layer arrangements can be employed. Thus, a transport layer can be positioned between two charge generation layers which can have the same or different respective compositions and layer thicknesses. Also, a charge generation layer can be positioned between two charge-transport layers only one of which may contain a compound of Formula I or Formula IX.

The exemplary embodiment has been described with reference to the various specific embodiments. Obviously, modifications and alterations will occur to others upon reading and understanding the preceding detailed description. It is intended that the exemplary embodiment be construed as including all such modifications and alterations insofar as they come within the scope of the appended claims or the equivalents thereof.

The invention claimed is:

1. A compound of Formula IX

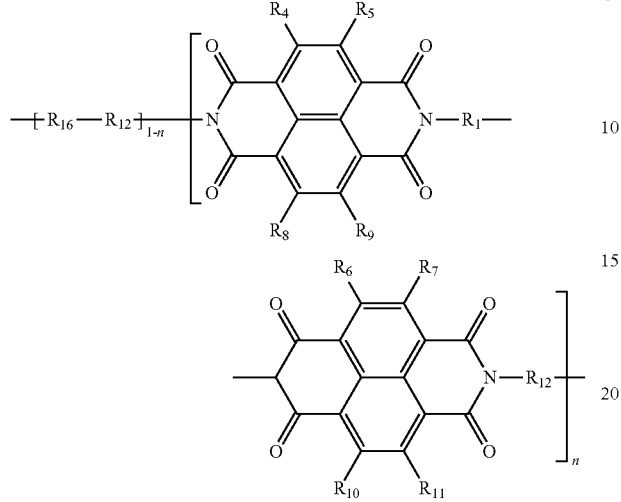

wherein $R_1$ is independently selected from the group consisting of a hetero atom containing group, a hydrocarbon containing group, and a hydrocarbon group substituted at least once with a hetero atom moiety;

$R_{16}$ is independently selected from the group consisting of a nitrogen containing group, a sulfur containing group, a hydroxyl group, a silicon containing group, hydrogen, a halogen, a hetero atom containing group, a hydrocarbon group and a substituted hydrocarbon group;

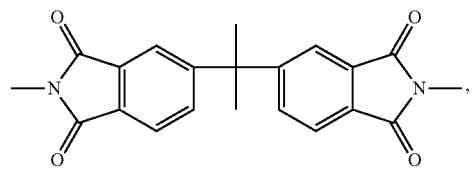

(a)

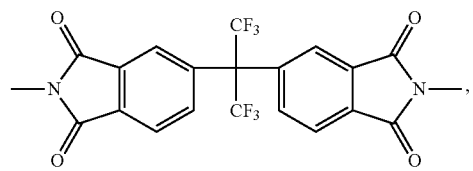

(b)

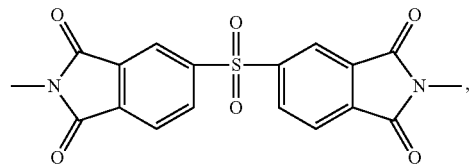

(c)

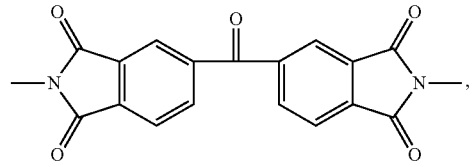

(d)

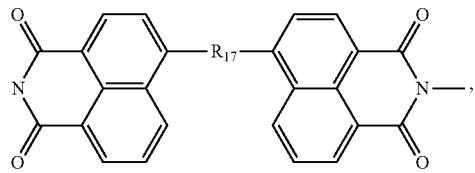

(e)

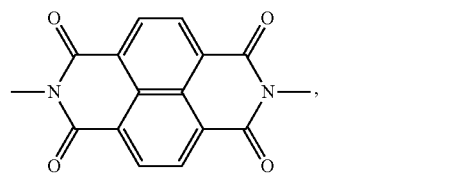

(f)

(g)

(h)

(i)

(j)

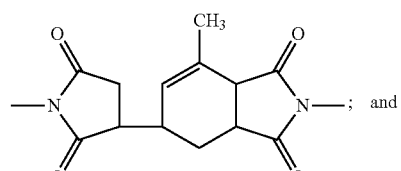

(k)

wherein $R_{12}$ and $R_{17}$ is independently selected from the group consisting of a nitrogen containing group, a sulfur containing group, a hydroxyl group, a silicon containing group, hydrogen, a halogen, a hetero atom containing group, a hydrocarbon group and a substituted hydrocarbon group; and $R_4$, $R_5$, $R_6$, $R_7$, $R_8$, $R_9$, $R_{10}$, and $R_{11}$ are independently selected from the group consisting of a nitrogen containing group, a sulfur containing group, a hydroxyl group, a silicon containing group, hydrogen, a halogen, a hetero atom containing group, a hydrocarbon group, and a hydrocarbon group that is substituted at least once with a hetero atom moiety; and n is a fraction between 0 and 1.

2. The compound according to claim 1, wherein $R_4$, $R_5$, $R_6$, $R_7$, $R_8$, $R_9$, $R_{10}$, and $R_{11}$ are hydrogen.

3. The compound according to claim 2, wherein $R_1$ is selected from the group consisting of a straight chain alkyl group and a branched alkyl group.

4. The compound according to claim 1, wherein $R_1$ is selected from the group consisting of a straight chain alkyl group and a branched alkyl group, and $R_4$, $R_5$, $R_6$, $R_7$, $R_8$, $R_9$, $R_{10}$, and $R_{11}$ are hydrogen.

5. The compound of claim 1, wherein $R_1$ is selected from the group consisting of an alkoxy group having from about 3 to about 30 atoms, a heterocyclic system having from about 11 to about 30 atoms; and an alkoxyaryl having from about 7 to about 30 atoms.

6. The compound of claim 1, wherein $R_1$ is selected from the group consisting of a straight chain alkyl group having from 1 to about 30 carbon atoms, a branched alkyl group having from about 3 to about 30 carbon atoms, a cycloalkyl group having from about 3 to about 20 carbon atoms, a monocyclic aromatic group, a polycyclic aromatic group having from about 11 to about 30 carbon atoms, an alkylaryl group having from about 7 to about 30 carbon atoms, and an arylalkyl group having from about 7 to about 30 carbon atoms.

7. The compound of claim 1, wherein n is a weight fraction from about 0.01 to about 0.85.

8. The compound of claim 1, wherein n is a weight fraction from about 0.20 to about 0.50.

\* \* \* \* \*